(12) United States Patent
Newman

(10) Patent No.: US 10,561,365 B2
(45) Date of Patent: Feb. 18, 2020

(54) SYSTEM AND METHOD OF MONITORING CONDITION OF EQUINES

(71) Applicant: SCR ENGINEERS LTD, Netanya (IL)

(72) Inventor: Elizabeth Newman, Kibbutz Givat Brenner (IL)

(73) Assignee: SCR ENGINEERS LTD, Netanya (IL)

( * ) Notice: Subject to any disclaimer, the term of this patent is extended or adjusted under 35 U.S.C. 154(b) by 1065 days.

(21) Appl. No.: 14/895,219

(22) PCT Filed: Nov. 30, 2014

(86) PCT No.: PCT/IL2014/051038
§ 371 (c)(1),
(2) Date: Dec. 2, 2015

(87) PCT Pub. No.: WO2015/083153
PCT Pub. Date: Jun. 11, 2015

(65) Prior Publication Data
US 2016/0100802 A1    Apr. 14, 2016

Related U.S. Application Data

(60) Provisional application No. 61/910,440, filed on Dec. 2, 2013, provisional application No. 62/068,770, filed on Oct. 27, 2014.

(51) Int. Cl.
*A61B 5/00* (2006.01)
*A61B 5/117* (2016.01)
(Continued)

(52) U.S. Cl.
CPC .......... *A61B 5/6831* (2013.01); *A01K 29/005* (2013.01); *A61B 5/0022* (2013.01);
(Continued)

(58) Field of Classification Search
CPC ........ G16H 10/60; A01K 29/005; A61B 5/08; A61B 5/00; A61B 5/0205
See application file for complete search history.

(56) References Cited

U.S. PATENT DOCUMENTS 6,536,377 B2   3/2003   Beaver
8,166,923 B2   5/2012   Davies
(Continued)

FOREIGN PATENT DOCUMENTS

WO    2011/120529    10/2011
WO    2015/083153    6/2015

OTHER PUBLICATIONS

International Search Report of PCT/IL2014/051038, dated Sep. 16, 2015.
Written Opinion of PCT/IL2014/051038, dated Sep. 16, 2015.

*Primary Examiner* — Regis J Betsch
*Assistant Examiner* — Jeremy A Delozier

(57) ABSTRACT

A system for behavioral monitoring for equines, comprising at least one sensor to measure a signal related to the equine, a database to store at least one parameter of the equine as a function of time, and processing means. The sensor is in communication with the equine, and comprises a wireless transmitter which is in communication with the database. The processing means, in communication with the database, is adapted to (i) determine, from at least one signal from the at least one sensor, at least one parameter of the equine as a function of time; (ii) establish normal behavior of the equine based on the parameter; and (iii) identify at least one abnormal behavior of the equine by identifying at least one deviation from normal behavior.

16 Claims, 22 Drawing Sheets

(51) Int. Cl.
*A61B 5/20* (2006.01)
*A61B 5/11* (2006.01)
*A01K 29/00* (2006.01)
*A61B 5/0205* (2006.01)

(52) U.S. Cl.
CPC .......... *A61B 5/02055* (2013.01); *A61B 5/117* (2013.01); *A61B 5/1123* (2013.01); *A61B 5/201* (2013.01); *A61B 5/4255* (2013.01); *A61B 5/4812* (2013.01); *A61B 5/7282* (2013.01); *A61B 5/742* (2013.01); *A61B 5/7405* (2013.01); *A61B 5/746* (2013.01); *A61B 2503/40* (2013.01); *A61B 2560/0242* (2013.01)

(56) References Cited

U.S. PATENT DOCUMENTS

| | | | | |
|---|---|---|---|---|
| 2001/0050062 | A1* | 12/2001 | Isley | A01K 29/00 119/712 |
| 2006/0106289 | A1 | 5/2006 | Elser et al. | |
| 2008/0255468 | A1* | 10/2008 | Derchak | A61B 5/0205 600/529 |
| 2010/0179454 | A1* | 7/2010 | Davies | A01K 11/008 600/595 |
| 2010/0302004 | A1* | 12/2010 | Winstead | A01K 29/005 340/7.32 |
| 2013/0211773 | A1* | 8/2013 | Loeschinger | A61B 5/1121 702/141 |

* cited by examiner

A          B

SYSTEM AND METHOD OF MONITORING CONDITION OF EQUINES

FIELD OF THE INVENTION

The present invention generally pertains to a system and method for monitoring any abnormality in equine; e.g., identifying changes in the health-condition of equines, any change in the equines' normal behavior, detecting illness, allergies, colic, lack of sleep or too much sleep, and identifying getting cast.

BACKGROUND OF THE INVENTION

The present invention generally pertains to a system and method for monitoring any abnormality in an equine; e.g., identifying changes in the health-condition of equines, any change in the equines' normal behavior, detecting illness, allergies, colic, lack of sleep or too much sleep, and identifying getting cast.

Equines, particularly horses, can be prone to e.g., colic, which is the leading cause of death in horses; the incidence of colic in the general horse population has been estimated as between 10 and 11 percent on an annual basis. Even when not fatal, colic can be very uncomfortable for the horse and can be debilitating.

Prevalence of colic can be reduced by using care in the choice of feed for the horse and by ensuring that the animal has proper exercise. However, over 80% of colic cases in horses are idiopathic, i.e., with no known cause, meaning that colic very often strikes without warning, making early treatment difficult, especially if the colic strikes when the horse is in a large paddock or if the colic strikes at night.

Colic in a racehorse severe enough to need surgical intervention results, in the vast majority of cases, in the racehorse never properly recovering its form; the horse never again wins races.

U.S. Pat. No. 8,166,923 to Davies discloses an approach to monitoring, evaluation, diagnosis, treatment or conditioning of animals such as horses that does not require use of restrictive equipment such as treadmills or force plates and that can provide either or both of more or less immediate or continuous processing of data to perform the monitoring or diagnosis. One or more wireless sensors are attached to the animal, for example, to measure motion-related parameter associated with one or more parts of the animal. Sensor data is received from the sensors and processed to identify a characteristic of the motion of the animal, such as a quality of gait. The sensor data can also be used to avoid injury to the animal and/or the rider, and to verify the identity of an animal.

However Davies discloses sensors able to determine aspects of the gait of the animal by determining aspects of the motion of the animal's limbs, but does not determine the position of the animal.

U.S. Pat. No. 6,536,377 to Beaver discloses a system for detecting the relative inverted posture of an equine specimen. When such a posture, or positional attitude, of an equine specimen is greater than 90 degrees but less than 270 degrees as measured with respect to the rotation of the animal's body around the lateral axis—anterior to posterior—whereby the normal standing position of the animal is zero degrees, then a sensing switch will activate and transmit a corresponding radio frequency signal to a receiver at a remote location and sound an alarm to alert monitoring personnel.

However, the system of Beaver does not include a database of normal equine behavior, nor does it include recording of the behavior of the monitored animal, nor does it include any comparison of the animal's current behavior with either previous behavior by the same animal or by other animals. Furthermore, the system of Beaver can not distinguish between an animal rolling for pleasure or to scratch its back, and an animal rolling in pain.

It is therefore a long felt need to provide a system that can be mounted on the body of an equine for monitoring its behavior pattern and comparing said behavior pattern to the normal behavior of either that animal or other animals.

SUMMARY OF THE INVENTION

It is an object of the present invention to disclose a system for monitoring a parameter of an equine and determining therefrom such items as illness in the equine, any deviation from the equine's normal behavior, e.g., colic, getting cast, not getting sufficient sleep, and sleeping too much.

It is another object of the present invention to disclose a system for behavioral monitoring for equines, comprising: (a) at least one first sensor, comprising at least one first wireless transmitter; said at least one first sensor is in communication with said equine; (b) a database in communication with said at least one first transmitter, said database adapted to store at least one parameter of said equine as a function of time; and, (c) processing means in communication with said database, said processing means adapted to (i) determine, from at least one signal from said at least one sensor, said at least one parameter of said equine as a function of time; (ii) establish normal behavior of said equine based on said parameter of said equine as a function of time; and (iii) identify at least one abnormal behavior of said equine by identifying at least one deviation from said normal behavior.

It is another object of the present invention to disclose the system, wherein said at least one first sensor is located in a position selected from a group consisting of: the girth of the equine, the head of the equine, the neck of the equine, the withers of the equine, a leg of the equine, the rump of the equine, and any combination thereof.

It is another object of the present invention to disclose the system, wherein said parameter is selected from a group consisting of position of at least a portion of said equine, movement of at least a portion of said equine, sound pattern made by said equine, temperature of said equine, pulse rate of said equine, movement of said equine, oxygen level of said equine, $CO_2$ level of said equine, sweating of said equine, sound pattern in said equine's environment and any combination thereof.

It is another object of the present invention to disclose the system, wherein said at least one position of said equine is selected from a group consisting of (a) equine standing and feeding; (b) equine lying down with head up; (c) equine recumbent; (d) equine rolling, (e) equine rearing, (f) equine bucking, and (g) any combination thereof.

It is another object of the present invention to disclose the system, wherein said abnormal behavior is selected from colic, silent colic, getting cast, silent cast, undiagnosed injury, not getting sufficient sleep, sleeping too much, abnormal sweating, temperature too high, temperature too low, oxygen level too high, oxygen level too low, $CO_2$ level too low, $CO_2$ level too high, rearing, bucking, moving too much, moving too little, eating too much, eating too little, chewing objects other than food, drinking too much, drinking too little, uttering an abnormal sound pattern and any combination thereof.

It is another object of the present invention to disclose the system, wherein colic is identifiable by behavior selected from a group consisting of: repeated rolling and getting up, lying down and getting up repeatedly without rolling, periodic rolling, and any combination thereof.

It is another object of the present invention to disclose the system, wherein repeated rolling and getting up consists of rolling and getting up more than a first predetermined number of times during a first predetermined period of time.

It is another object of the present invention to disclose the system, wherein lying down and getting up repeatedly without rolling, consists of lying down and getting up without rolling more than a second predetermined number of times in a second predetermined period of time.

It is another object of the present invention to disclose the system, wherein periodic rolling consists of rolling from a position lying down with head up or from a recumbent position such that said episodes of rolling exceed a predetermined amount of time in a third predetermined period of time.

It is another object of the present invention to disclose the system, wherein getting cast is identifiable by prolonged rolling.

It is another object of the present invention to disclose the system, wherein said prolonged rolling is rolling such that there are more than a fourth predetermined number of episodes of rolling in a fourth predetermined period of time.

It is another object of the present invention to disclose the system, wherein getting cast is identifiable by the equine rolling only from a position selected from a group consisting of lying down with head up and recumbent.

It is another object of the present invention to disclose the system, wherein said condition of not getting sufficient sleep consists of the equine consistently averaging less than a predetermined minimum amount of REM sleep per night.

It is another object of the present invention to disclose the system, wherein said condition of sleeping too much consists of said equine consistently averaging more than a predetermined maximum amount of REM sleep per night.

It is another object of the present invention to disclose the system, wherein said sound pattern made by said equine is selected from a group consisting of: eating pattern, coughing pattern, neighing pattern, whinnying pattern, squealing pattern, snorting pattern, sighing pattern, other vocalizing patterns, wheezing pattern, pattern of hoof sounds from contact with the floor, pattern of hoof sounds from contact with the equine's bedding, pattern of hoof sounds from contact with the walls of the box, pattern of hoof sounds from contact with feeding apparatus, pattern of head shaking, urinating pattern, defecating pattern and any combination thereof.

It is another object of the present invention to disclose the system, wherein said coughing pattern is selected from a group consisting of: the frequency of coughing, the duration of individual coughs, the duration of a series of coughs, the loudness of coughs, coughing comprising wet coughs, coughing comprising dry coughs, the time of day of the coughing, the movement pattern of the equine at the time of the coughing, and any combination thereof.

It is another object of the present invention to disclose the system, wherein said abnormal sound pattern is selected from a group consisting of: coughing too often, coughing too seldom, individual coughs of too short duration, individual coughs of too long duration, too short a series of coughs, too long a series of coughs, overly loud coughs, overly quiet coughs, wet coughing, persistent dry coughing, coughing at an unusual time of day, increased coughing at a particular time of day, coughing during exercise, coughing in the stable, coughing in the aftermath of exercise, coughing in the lead-up to exercise, coughing during prolonged exercise, coughing in the aftermath of prolonged exercise, coughing during prolonged exercise, coughing in the aftermath of prolonged exercise, coughing while stabled, coughing while in the pasture, and any combination thereof.

It is another object of the present invention to disclose the system, wherein said abnormal sound pattern is selected from a group consisting of: eating too fast, eating too slowly, spending too little time eating; spending too much time eating; eating too little, eating too much, chewing without eating, chewing on objects other than food, biting on objects other than food; drinking too much; drinking too little, drinking too fast, drinking too slowly, wheezing and any combination thereof.

It is another object of the present invention to disclose the system, wherein said sound pattern in said equine's environment is selected from a group consisting of: breathing, hoof sounds, neighing, whinnying, squealing, snorting, sighing, otherwise vocalizing, eating, moving, urinating, defecating, non-equine animal vocalizing, footsteps, human speech, human whistling, human humming, human singing, mechanical sounds, weather sounds, and any combination thereof.

It is another object of the present invention to disclose the system, wherein said non-equine animal vocalizing is selected from a group consisting of: barking, growling, yapping, meowing, purring, hissing, mooing, lowing, groaning, and any combination thereof.

It is another object of the present invention to disclose the system, wherein said abnormal sound pattern is selected from a group consisting of: hooves hitting the floor too much, hooves hitting the floor too little, hooves hitting the bedding too much, hooves hitting the bedding too little, hooves hitting walls too much, hooves hitting objects too much, hooves hitting objects too little, and any combination thereof.

It is another object of the present invention to disclose the system, wherein reduction of said abnormal behavior pattern is a determinant of fitness to resume full work.

It is another object of the present invention to disclose the system, wherein said abnormal behavior pattern is selected from a group consisting of: an abnormal REM sleep pattern, an abnormal non-REM sleep pattern, a abnormal feeding pattern, an abnormal rolling pattern and any combination thereof.

It is another object of the present invention to disclose the system, wherein said abnormal behavior indicates said equine's health status.

It is another object of the present invention to disclose the system, wherein said equine's health status is obtainable from the coughing pattern of said equine.

It is another object of the present invention to disclose the system, wherein said coughing pattern is selected from a group consisting of: the frequency of coughing, the duration of individual coughs, the duration of a series of coughs, the loudness of coughs, coughing comprising wet coughs, coughing comprising dry coughs, the time of day of the coughing, the movement pattern of the equine at the time of the coughing, and any combination thereof.

It is another object of the present invention to disclose the system, wherein said coughing pattern is indicative of at least one selected from a group consisting of a viral infection, a bacterial infection, recovering from a bacterial infection, chronic respiratory disease, allergic reaction, accumulation of mucus, a foreign object lodged in the airway, and any combination thereof.

It is another object of the present invention to disclose the system, wherein said abnormal behavior indicates change in said equine's anxiety status.

It is another object of the present invention to disclose the system, herein said change in said equine's anxiety status is selected from a group consisting of raised anxiety and lowered anxiety.

It is another object of the present invention to disclose the system, wherein said indicator of raised anxiety is selected from a group consisting of: raising of the head, a general bracing of muscles, increased respiration, widening of the eye, fixation on an object, uneven twisting of facial muscles and any combination thereof.

It is another object of the present invention to disclose the system, wherein said indicator of lowered anxiety is selected from a group consisting of: the lick-chew-swallow reflex, lowering the head, blinking the eyes, blowing off held breath or giving an audible sigh, licking and chewing, relaxation about the eyes and ears and muzzle, cocking a hind leg in a relaxed rather than threatening posture, and any combination thereof.

It is another object of the present invention to disclose the system, wherein said sensor comprises a member of a group consisting of: an accelerometer, a motion sensor, a sound sensor, an oxygen sensor, a $CO_2$ sensor, a pressure sensor, a velocity sensor, a temperature sensor, a moisture sensor, a stress sensor and any combination thereof.

It is another object of the present invention to disclose the system, wherein said accelerometer is selected from a group consisting of: a MEMS accelerometer, a piezoelectric accelerometer, a piezoresistive accelerometer, a capacitive accelerometer, a hot air bubble accelerometer, an optical accelerometer and any combination thereof.

It is another object of the present invention to disclose the system, wherein said motion sensor is selected from a group consisting of: a MEMS motion sensor, a glass cell holding electrodes and a drop of mercury, a metal ball that creates an electromagnetic field when changing, an infrared detector, a visible light detector, an acoustic detector and any combination thereof.

It is another object of the present invention to disclose the system, wherein said sound sensor is selected from a group consisting of: a diaphragm-type microphone, a piezoelectric device and any combination thereof.

It is another object of the present invention to disclose the system, further comprising a harness selected from a group consisting of: an elasticated surcingle adapted to encircle the girth of said equine, a halter on said equine's head, a hoof boot, a horse rug, a saddle pad, a saddle, a fly mask, a cinch, a leg protector, a leg wrap, a leg bandage, and any combination thereof.

It is another object of the present invention to disclose the system, wherein said sensor is attachable to said harness.

It is another object of the present invention to disclose the system, wherein said attachment is reversible.

It is another object of the present invention to disclose the system, further comprising a warning mechanism in communication with said processing means.

It is another object of the present invention to disclose the system, wherein said warning mechanism is in wireless or wired communication with said processing means.

It is another object of the present invention to disclose the system, wherein said warning mechanism provides notification of a member of a group consisting of: said abnormal behavior in said equine, said abnormal environment, and any combination thereof.

It is another object of the present invention to disclose the system, wherein said warning mechanism is selected from a group consisting of an audible alarm; a visual alarm; a message sent to at least one person; and any combination thereof.

It is another object of the present invention to disclose the system, wherein said audible alarm is selected from a group consisting of: a constant-pitch sound, a variable-pitch sound, a constant-volume sound, a ringing sound, a buzzing sound, a voice message, a variable-volume sound, and any combination thereof.

It is another object of the present invention to disclose the system, wherein said visual alarm is selected from a group consisting of: an illuminated light, a visible picture, a constant-color light, a variable-color light, a constant-brightness, a variable-brightness light, and any combination thereof.

It is another object of the present invention to disclose the system, wherein said message is selected from a group consisting of an audible telephone message, an SMS message, a message displayed on a display and any combination thereof.

It is another object of the present invention to disclose the system, additionally comprising an ID, said ID uniquely identifying said equine.

It is another object of the present invention to disclose the system, wherein said system additionally comprises at least one second sensor in communication with said equine; said second sensor comprising at least one second wireless transmitter; said database adapted to store at least one parameter selected from a group consisting of: a parameter of said equine's environment, a parameter of said equine's environment as a function of time, and any combination thereof.

It is another object of the present invention to disclose the system, wherein said first sensor and said second sensor are integrated together.

It is another object of the present invention to disclose the system, wherein said first transmitter and said second transmitter are integrated together.

It is another object of the present invention to disclose the system, wherein said processing means are further adapted to establish a member of a group consisting of a normal environment of said equine, and a normal environment of said equine as a function of time.

It is another object of the present invention to disclose the system, wherein said processing means are further adapted to identify an abnormal environment by identifying a member of a group consisting of: any deviation from said normal environment, and any said time-related deviation from said normal environment.

It is another object of the present invention to disclose the system, wherein a trigger for said abnormal behavior is identifiable as said deviation from said normal environment or said time-related deviation from said normal environment.

It is another object of the present invention to disclose a method for monitoring behavior of equines, comprising steps of: (a) providing a system for behavioral monitoring for equines, comprising: (i) at least one first sensor comprising at least one first wireless transmitter; said at least one first sensor in communication with said equine; (ii) a database in communication with said at least one first transmitter, said database adapted to store at least one parameter of said equine as a function of time; and, (iii) processing means in communication with said database, said processing means adapted to (1) determine, from at least one signal from said at least one sensor, said at least one parameter of said equine as a function of time; (2) establish normal behavior of said equine based on said parameter of said equine as a function of time; and (3) identify at least one abnormal behavior of said equine by identifying at least one deviation from said normal behavior; (b) positioning said first sensor in communication with said equine; (c) determining said parameter of said equine from said sensor's signal; (d) storing said parameter of said equine in said database as a function of time; (e) establishing said normal behavior of said equine; and (f) identifying said deviation from said normal behavior, thereby identifying said abnormal behavior.

It is another object of the present invention to disclose the method, additionally comprising step of locating said at least one first sensor in a position selected from a group consisting of: the girth of the equine, the head of the equine, the neck of the equine, the withers of the equine, a leg of the equine, the rump of the equine, and any combination thereof.

It is another object of the present invention to disclose the method, additionally comprising step of selecting said parameter from a group consisting of position of at least a portion of said equine, movement of said equine, sound pattern made by said equine, temperature of said equine, pulse rate of said equine, movement of said equine, oxygen level of said equine, $CO_2$ level of said equine, sweating of said equine, sound pattern in said equine's environment and any combination thereof.

It is another object of the present invention to disclose the method, additionally comprising step of selecting said at least one position of said equine from (a) equine standing and feeding; (b) equine lying down with head up; (c) equine recumbent; (d) equine rolling, (e) equine rearing, (f) equine bucking, and (g) any combination thereof.

It is another object of the present invention to disclose the method, additionally comprising step of selecting said behavior from a group consisting of colic, silent colic, getting cast, silent cast, undiagnosed injury, not getting sufficient sleep, sleeping too much, abnormal sweating, temperature too high, temperature too low, oxygen level too high, oxygen level too low, $CO_2$ level too low, $CO_2$ level too high, rearing, bucking, moving too much, moving too little, eating too much, eating too little, chewing objects other than food, drinking too much, drinking too little, uttering an abnormal sound pattern, and any combination thereof.

It is another object of the present invention to disclose the method, additionally comprising step of identifying colic by behavior selected from a group consisting of: repeated rolling and getting up, lying down and getting up repeatedly without rolling, periodic rolling, and any combination thereof.

It is another object of the present invention to disclose the method, additionally comprising step of identifying repeated rolling and getting up as behavior consisting of rolling and getting up more than a first predetermined number of times during a first predetermined period of time.

It is another object of the present invention to disclose the method, additionally comprising step of identifying lying down and getting up repeatedly without rolling as lying down and getting up without rolling more than a second predetermined number of times in a second predetermined period of time.

It is another object of the present invention to disclose the method, additionally comprising step of identifying periodic rolling as rolling from a position lying down with head up or from a recumbent position such that said episodes of rolling exceed a predetermined amount of time in a third predetermined period of time.

It is another object of the present invention to disclose the method, additionally comprising step of identifying getting cast by prolonged rolling.

It is another object of the present invention to disclose the method, additionally comprising step of identifying said prolonged rolling to be rolling such that there are more than a fourth predetermined number of episodes of rolling in a fourth predetermined period of time.

It is another object of the present invention to disclose the method, additionally comprising step of identifying getting cast by the equine rolling only from a position selected from a group consisting of lying down with head up and recumbent.

It is another object of the present invention to disclose the method, additionally comprising step of identifying said condition of not getting sufficient sleep by the equine consistently averaging less than a predetermined minimum amount of REM sleep per night.

It is another object of the present invention to disclose the method, additionally comprising step of specifying said condition of sleeping too much to be said equine consistently averaging more than a predetermined maximum amount of REM sleep per night.

It is another object of the present invention to disclose the method, additionally comprising step of selecting said sound pattern made by said equine from a group consisting of: eating pattern, coughing pattern, neighing pattern, whinnying pattern, squealing pattern, snorting pattern, sighing pattern, other vocalizing patterns, wheezing pattern, pattern of hoof sounds from contact with the floor, pattern of hoof sounds from contact with the equine's bedding, pattern of hoof sounds from contact with the walls of the box, pattern of hoof sounds from contact with feeding apparatus, pattern of head shaking, urinating pattern, defecating pattern and any combination thereof.

It is another object of the present invention to disclose the method, additionally comprising step of selecting said coughing pattern from a group consisting of: the frequency of coughing, the duration of individual coughs, the duration of a series of coughs, the loudness of coughs, coughing comprising wet coughs, coughing comprising dry coughs, the time of day of the coughing, the movement pattern of the equine at the time of the coughing, and any combination thereof.

It is another object of the present invention to disclose the method, additionally comprising step of selecting said abnormal sound pattern from a group consisting of: coughing too often, coughing too seldom, individual coughs of too short duration, individual coughs of too long duration, too short a series of coughs, too long a series of coughs, overly loud coughs, overly quiet coughs, wet coughing, persistent dry coughing, coughing at an unusual time of day, increased coughing at a particular time of day, coughing during exercise, coughing in the stable, coughing in the aftermath of exercise, coughing in the lead-up to exercise, coughing during prolonged exercise, coughing in the aftermath of prolonged exercise, coughing during prolonged exercise, coughing in the aftermath of prolonged exercise, coughing while stabled, coughing while in the pasture, and any combination thereof.

It is another object of the present invention to disclose the method, additionally comprising step of selecting said abnormal sound pattern from a group consisting of: eating too fast, eating too slowly, spending too little time eating;

spending too much time eating; eating too little, eating too much, chewing without eating, chewing on objects other than food, biting on objects other than food; drinking too much; drinking too little, drinking too fast, drinking too slowly, wheezing and any combination thereof.

It is another object of the present invention to disclose the method, additionally comprising step of selecting said sound pattern in said equine's environment from a group consisting of: breathing, hoof sounds, neighing, whinnying, squealing, snorting, sighing, otherwise vocalizing, eating, moving, urinating, defecating, non-equine animal vocalizing, footsteps, human speech, human whistling, human humming, human singing mechanical sounds, weather sounds and any combination thereof.

It is another object of the present invention to disclose the method, additionally comprising step of selecting said non-equine animal vocalizing from a group consisting of: barking, growling, yapping, meowing, purring, hissing, mooing, lowing, groaning, and any combination thereof.

It is another object of the present invention to disclose the method, additionally comprising step of selecting said abnormal sound pattern from a group consisting of: hooves hitting the floor too much, hooves hitting the floor too little, hooves hitting the bedding too much, hooves hitting the bedding too little, hooves hitting walls too much, hooves hitting objects too much, hooves hitting objects too little, and any combination thereof.

It is another object of the present invention to disclose the method, additionally comprising step of determining fitness to resume full work from reduction of said abnormal behavior.

It is another object of the present invention to disclose the method, additionally comprising step of selecting said abnormal behavior pattern from a group consisting of: an abnormal REM sleep pattern, an abnormal non-REM sleep pattern, a abnormal feeding pattern, an abnormal rolling pattern and any combination thereof.

It is another object of the present invention to disclose the method, additionally comprising step of indicating said equine's health status by said abnormal behavior.

It is another object of the present invention to disclose the method, additionally comprising step of obtaining said equine's health status from the coughing pattern of said equine.

It is another object of the present invention to disclose the method, additionally comprising step of selecting said coughing pattern from a group consisting of: the frequency of coughing, the duration of individual coughs, the duration of a series of coughs, the loudness of coughs, coughing comprising wet coughs, coughing comprising dry coughs, the time of day of the coughing, the movement pattern of the equine at the time of the coughing, and any combination thereof.

It is another object of the present invention to disclose the method, additionally comprising step of indicating from said coughing pattern a member of a group consisting of a viral infection, a bacterial infection, recovering from a bacterial infection, chronic respiratory disease, allergic reaction, accumulation of mucus, a foreign object lodged in the airway, and any combination thereof.

It is another object of the present invention to disclose the method, additionally comprising step of indicating change in said equine's anxiety status by said abnormal behavior. It is another object of the present invention to disclose the method, additionally comprising step of selecting said change in said equine's anxiety status from a group consisting of raised anxiety and lowered anxiety.

It is another object of the present invention to disclose the method, additionally comprising step of selecting said indicator of raised anxiety from a group consisting of: raising of the head, a general bracing of muscles, increased respiration, widening of the eye, fixation on an object, uneven twisting of facial muscles and any combination thereof.

It is another object of the present invention to disclose the method, additionally comprising step of selecting said indicator of lowered anxiety from a group consisting of: the lick-chew-swallow reflex, lowering the head, blinking the eyes, blowing off held breath or giving an audible sigh, licking and chewing, relaxation about the eyes and ears and muzzle, cocking a hind leg in a relaxed rather than threatening posture, and any combination thereof.

It is another object of the present invention to disclose the method, additionally comprising step of selecting said sensor from a group consisting of: an accelerometer, a motion sensor, a sound sensor, an oxygen sensor, a $CO_2$ sensor, a pressure sensor, a velocity sensor, a temperature sensor, a moisture sensor, a stress sensor and any combination thereof.

It is another object of the present invention to disclose the method, additionally comprising step of selecting said accelerometer from a group consisting of: a MEMS accelerometer, a piezoelectric accelerometer, a piezoresistive accelerometer, a capacitative accelerometer, a hot air bubble accelerometer, an optical accelerometer and any combination thereof.

It is another object of the present invention to disclose the method, additionally comprising step of selecting said motion sensor from a group consisting of: a MEMS motion sensor, a glass cell holding electrodes and a drop of mercury, a metal ball that creates an electromagnetic field when changing, an infrared detector, a visible light detector, an acoustic detector and any combination thereof.

It is another object of the present invention to disclose the method, additionally comprising step of selecting said sound sensor from a group consisting of: a diaphragm-type microphone, a piezoelectric device and any combination thereof.

It is another object of the present invention to disclose the method, additionally comprising step of providing a harness selected from a group consisting of: an elasticated surcingle adapted to encircle the girth of said equine, a halter on said equine's head, a hoof boot, a horse rug, a saddle pad, a saddle, a fly mask, a cinch, a leg protector, a leg wrap, a leg bandage, and any combination thereof.

It is another object of the present invention to disclose the method, additionally comprising step of attaching said sensor to said harness.

It is another object of the present invention to disclose the method, additionally comprising step of providing said attachment as a reversible attachment.

It is another object of the present invention to disclose the method, additionally comprising step of providing a warning mechanism in communication with said processing means.

It is another object of the present invention to disclose the method, additionally comprising step of characterizing said warning mechanism as being in wireless or wired communication with said processing means.

It is another object of the present invention to disclose the method, additionally comprising step of providing notification, via said warning mechanism, of a member of a group selected from: said abnormal behavior in said equine, said abnormal environment, and any combination thereof.

It is another object of the present invention to disclose the method, additionally comprising step of selecting said warning mechanism from a group consisting of an audible alarm; a visual alarm; a message sent to at least one person; and any combination thereof.

It is another object of the present invention to disclose the method, additionally comprising step of selecting said audible alarm from a group consisting of: a constant-pitch sound, a variable-pitch sound, a constant-volume sound, a ringing sound, a buzzing sound, a voice message, a variable-volume sound, and any combination thereof.

It is another object of the present invention to disclose the method, additionally comprising step of selecting said visual alarm from a group consisting of: an illuminated light, a visible picture, a constant-color light, a variable-color light, a constant-brightness, a variable-brightness light, and any combination thereof.

It is another object of the present invention to disclose the method, additionally comprising step of selecting said message from a group consisting of an audible telephone message, an SMS message, a message displayed on a display and any combination thereof.

It is another object of the present invention to disclose the method, additionally comprising step of providing an ID, said ID uniquely identifying said equine.

It is another object of the present invention to disclose the method, additionally comprising step of providing at least one second sensor in communication with said equine; said second sensor comprising at least one second wireless transmitter; said database adapted to store at least one parameter selected from a group consisting of: a parameter of said equine's environment, a parameter of said equine's environment as a function of time, and any combination thereof.

It is another object of the present invention to disclose the method, additionally comprising step of integrating together said first sensor and said second sensor.

It is another object of the present invention to disclose the method, additionally comprising step of integrating together said first transmitter and said second transmitter.

It is another object of the present invention to disclose the method, additionally comprising step of establishing, by means of said processing means, a member of a group consisting of a normal environment of said equine, and a normal environment of said equine as a function of time.

It is another object of the present invention to disclose the method, additionally comprising step of identifying, by means of said processing means, an abnormal environment by identifying a member of a group consisting of: any deviation from said normal environment, and any said time-related deviation from said normal environment.

It is another object of the present invention to disclose the method, additionally comprising step of identifying, as a trigger for said abnormal behavior, said deviation from said normal environment or said time-related deviation from said normal environment.

BRIEF DESCRIPTION OF THE FIGURES

In order to better understand the invention and its implementation in practice, a plurality of embodiments will now be described, by way of non-limiting example only, with reference to the accompanying drawings, wherein FIG. 1 schematically illustrates a device of the prior art.

DETAILED DESCRIPTION OF THE PREFERRED EMBODIMENTS

Figure 1:
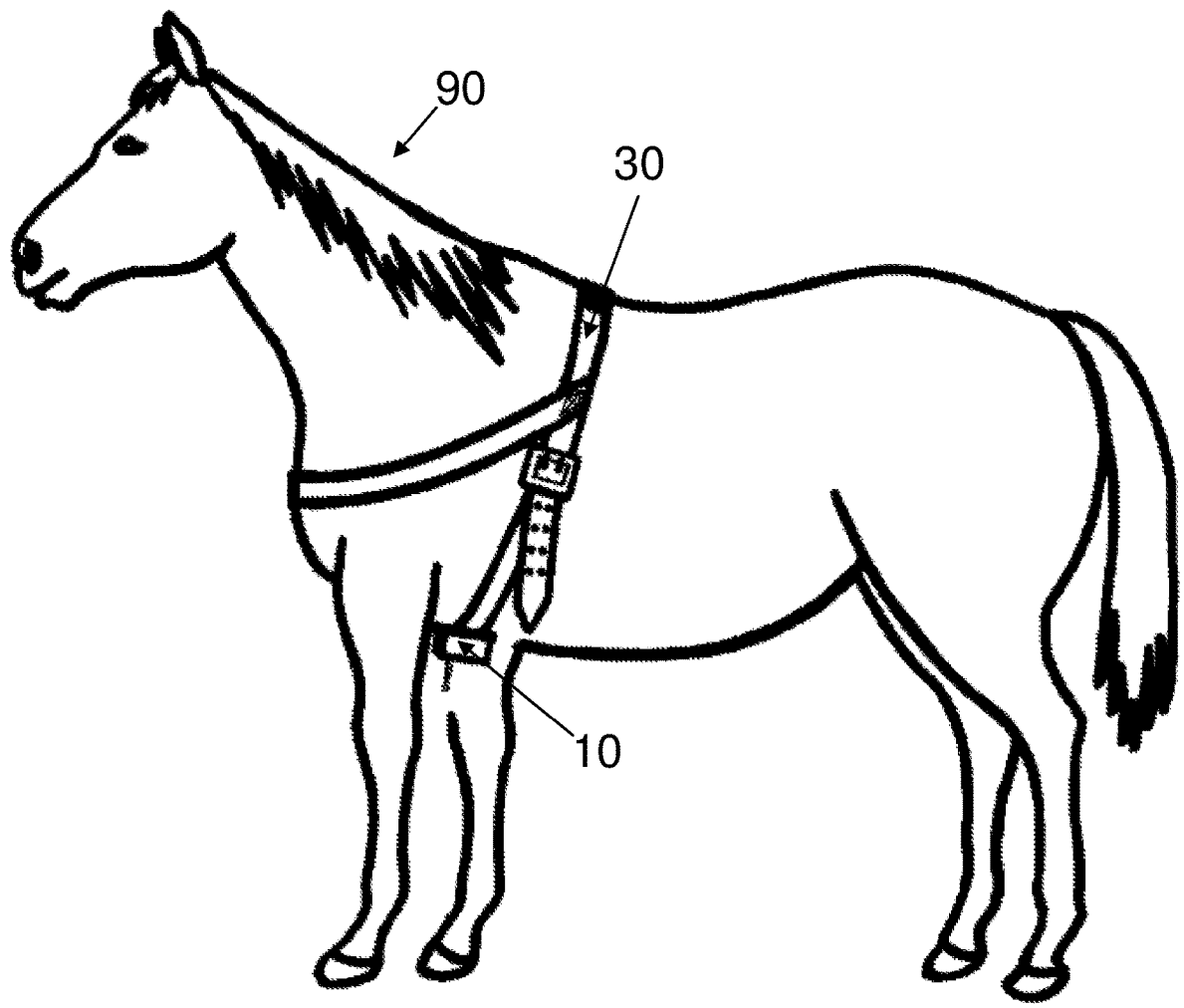

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for monitoring any abnormality in the activity of an equine.

Another object is to determine the health condition therefrom and behavior of said equine such as colic, getting cast, not getting sufficient sleep, and sleeping too much.

The term 'equine' hereinafter refers to any member of the genus equus, including horses, donkeys or asses, mules and zebras.

The term 'harness' hereinafter refers to any article of horse gear normally wearable by an equine. A harness can be, but is not limited to, a surcingle, a halter, a hoof boot, a horse rug, a saddle, a saddle pad, a fly mask, a cinch, a leg protector, a leg wrap, a leg bandage, and any combination thereof.

The term 'silent colic' hereinafter refers to an episode of colic that occurs when no human is present and which does not leave any obvious effect on the horse's condition or behavior. A typical silent colic would occur at night. The horse would exhibit normal behavior when shut into its stall for the night and, in the morning, would not show signs of distress or of having sweated during the night. No obvious change in its behavior would be apparent.

The term 'cast' refers to an equine becoming stuck against a stable wall. typically, it will become cast by rolling over in such a way that its body contacts the wall when its legs are in the air, or its legs become trapped between its body and the wall.

The term 'silent cast' hereinafter refers to an equine becoming cast when no human is present, when it spontaneously resolves the cast soon enough that the cast does not leave any obvious effect on the horse's condition or behavior. A typical silent cast would occur at night. The horse would exhibit normal behavior when shut into its stall for the night and, in the morning, would not show signs of distress or injury, nor would it show signs of having sweated during the night. No obvious change in its behavior would be apparent.

The term 'approximately' hereinafter refers to within 20% of a defined value.

The system of the present invention comprises at least one sensor preferably mounted on a horse by means of an article of horse gear, which will be referred to herein as a harness, a database adapted to store the sensor data, computing means adapted to determine a behavior pattern for the equine from the sensor data and compare the behavior pattern data to other behavior pattern data, said other data including, for non-limiting example, previous data for the same equine, data for another equine, or pooled data from a number of other equines, and communication means adapted to notify a user if any of the following occur: the type of behavior of the equine changes, the type of behavior differs from that of the comparison equine or equines, or the type of behavior becomes consistent with that of a specified previous behavior pattern of that equine, or of a specified behavior pattern of the comparison equine or equines.

In preferred embodiments, the sensor or sensors is attached, either fixedly or releasably, to a harness on the equine, as described hereinbelow. In other embodiments, the sensor can be directly attached to the equine, or implanted within the equine.

The portion of the system carried by the equine, whether on a harness, attached to the equine, or implanted on or within the equine, or otherwise persistently co-located with the equine, will be referred to as the "tag" or "tag system".

Identifiable behavior patterns include, but are not limited to, those of coughing, colic, getting cast, lack of sufficient REM sleep, an excess of REM sleep, heat stress, heat stroke, and stereotypical behavior.

Illness in the equine can be detected by changes in its behavior pattern, such as changes in the time spent feeding or changes in its coughing pattern.

In some embodiments, triggers for abnormal behavior of the equine can be determined from abnormalities or unusual events in the animal's environment. Such abnormalities or unusual events in the equine's environment include, but are not limited to, abnormal behavior of other equines, the abnormal presence of other animals, the abnormal behavior of other animals (a dog growling, for example), unusual environmental sounds, such as high winds, and unusual or abnormal mechanical sounds, such as drills or doors opening at night or breaking glass, or other unusual or abnormal sounds such as, but not limited to, human sounds such as speech at unusual hours, such as at night.

FIG. 1 shows an embodiment of a device of the prior art. In the prior art, a harness (30) holds the device (10) in position on the horse (90). The device comprises a switch which closes if the horse assumes an inverted position, so that, when the animal rolls or attempts to roll, the gravitational sensing switch within the sensor closes and activates the radio-frequency transmitter, which wirelessly transmits the animal's inverted posture condition to a remote location. The device has two modes of operation, a single-event single-alarm mode, where an alarm is activated for the duration of the rolling event, and a single-event continuous-alarm mode, where the alarm is activated by a single event and remains activated until reset at the monitor, even though the animal has righted itself, so that monitoring personnel are notified of the event even if they are not present when the event occurs.

Figure 2A:
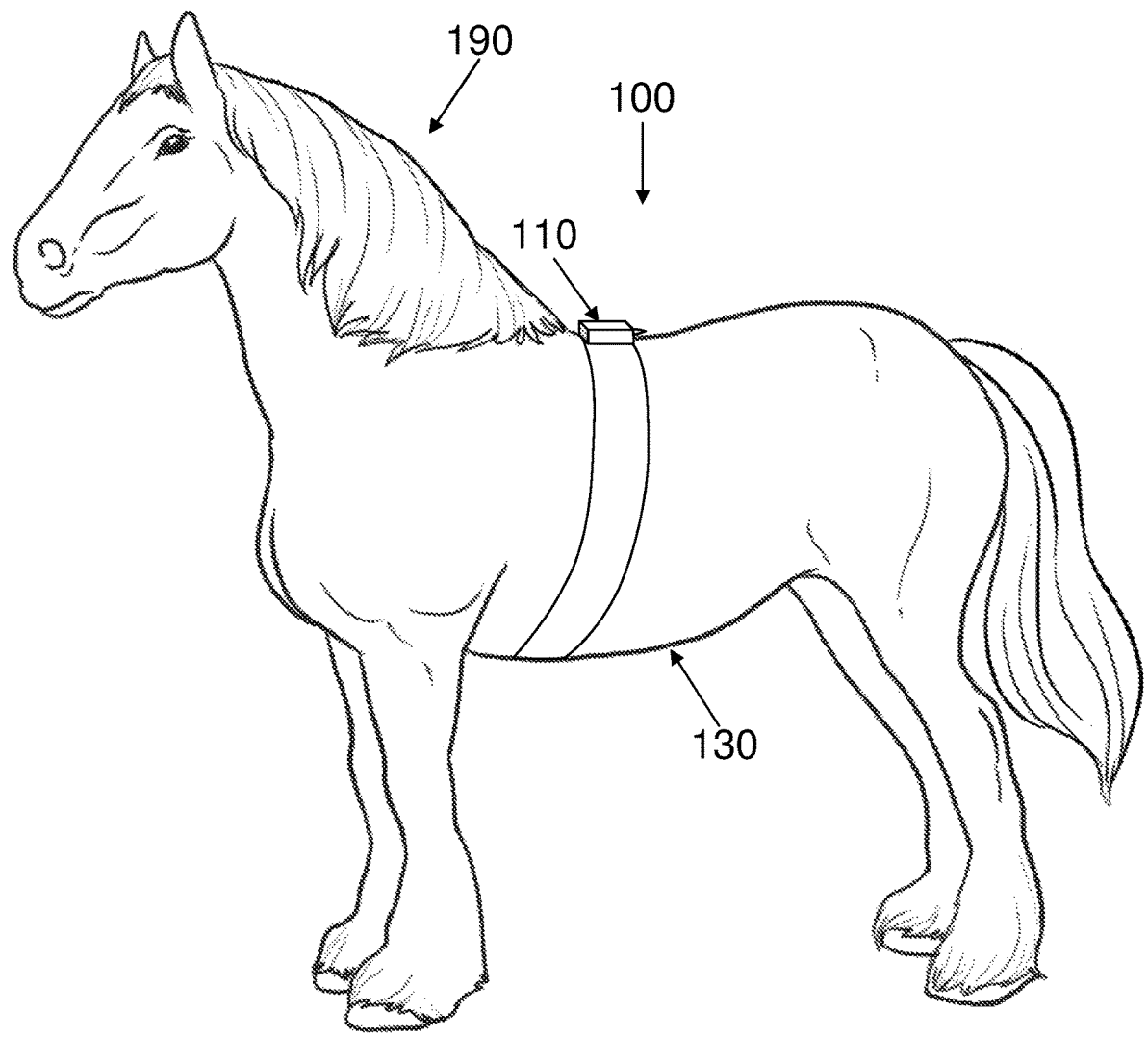
FIG. 2A-C schematically illustrates the present invention, in position on an equine.
Figure 2B:
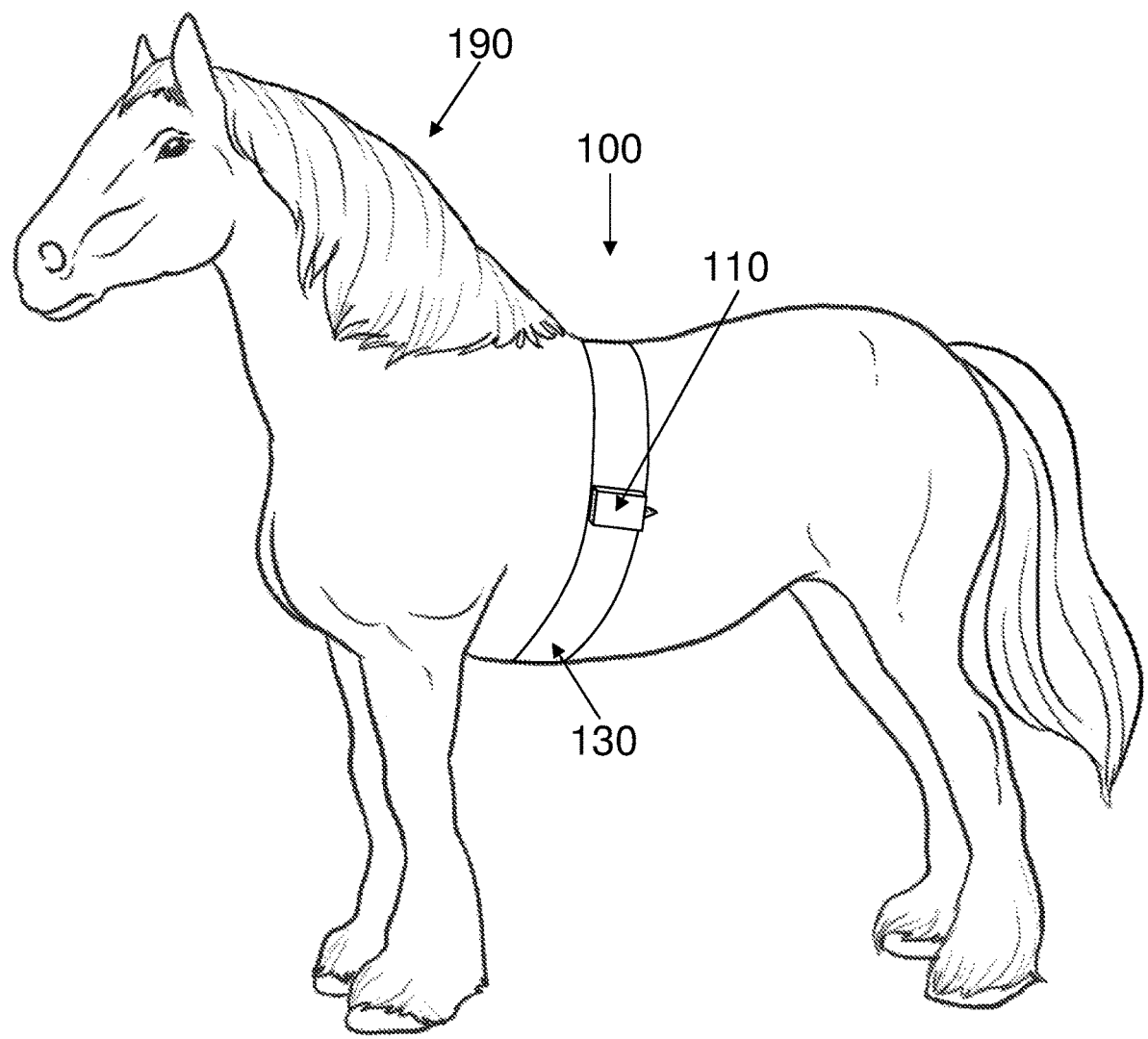
Figure 2C:
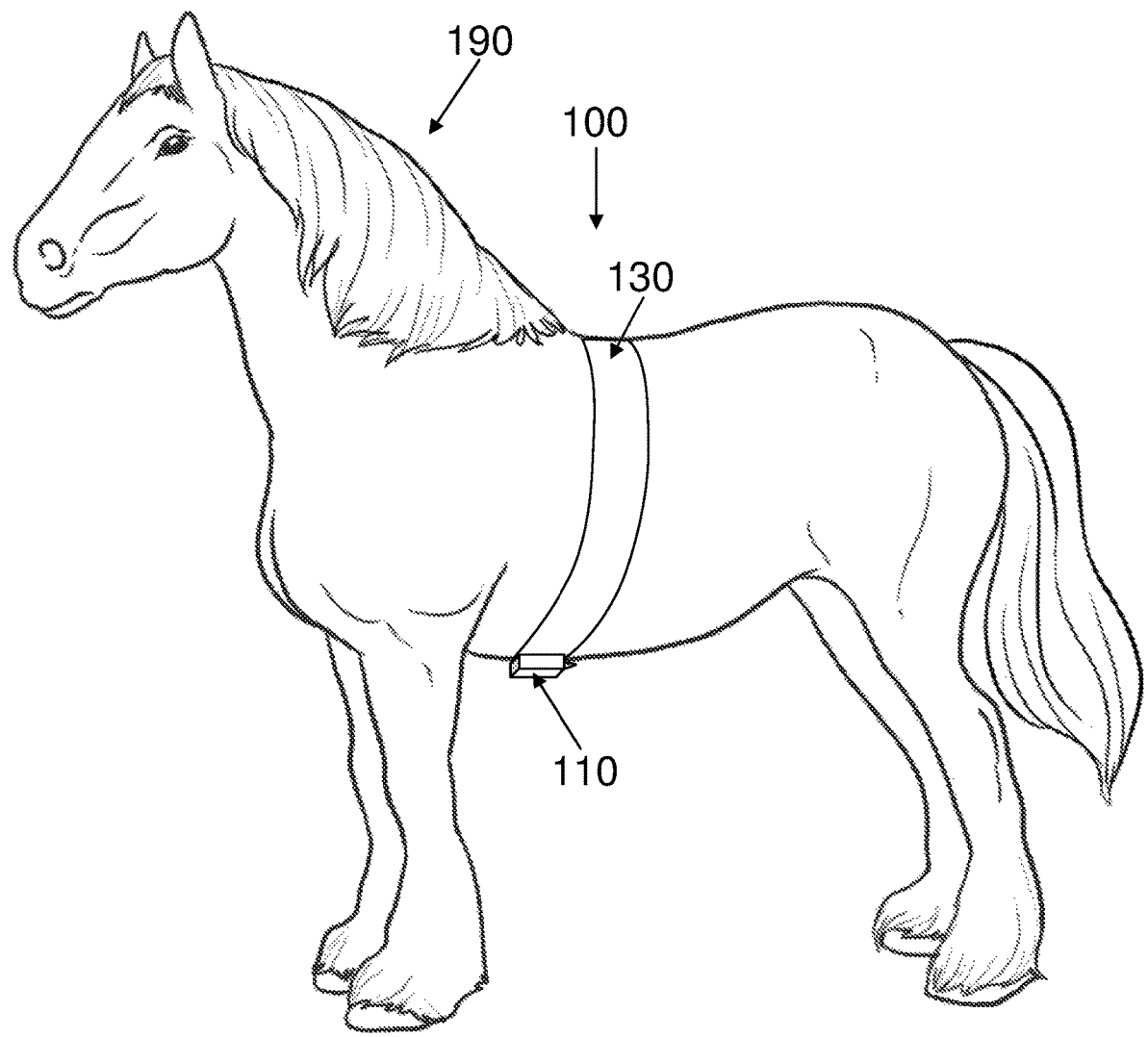

A schematic of an exemplary embodiment of the present system is shown in FIG. 2A-C. The system (100) comprises a sensor system (110) comprising at least one and preferably several sensors. The sensors can be, but are not limited to, accelerometers; motion sensors; sound sensors; gas sensors such as oxygen sensors or $CO_2$ sensors; pulse sensors other than motion sensors such as, but not limited to, velocity sensors or pressure sensors; temperature sensors; moisture sensors (to determine sweating); heartbeat sensors other than pulse sensors, stress sensors and any combination thereof. The sensor system (110) is adapted for wireless communication with a monitor (not shown). The sensor system is attachable to a harness (130), described hereinbelow.

In preferred embodiments, the sensors are Micro Electro Mechanical System (MEMS) sensors, to minimize the size of the tag system.

In preferred embodiments, the system will comprise an accelerometer and motion sensor, preferably as part of the same MEMS sensor; in other embodiments more than one MEMS sensor can be used. In some embodiments, the system comprises more than one accelerometer; in some embodiments, it comprises more than one motion sensor.

Motion sensors can also determine motion of the chest wall to determine breathing rates and the depth of breaths, jaw and lip motion, which can also determine chewing rates, movement of the eyelids, movement of the limbs, and any combination thereof.

The harness (130) is adapted to hold the device in position on the equine. In this embodiment, the harness encircles the girth of the equine. In other embodiments, the sensor system or tag can be attached to a harness on the head of the equine, on the neck of the equine, on the withers of the equine, on the legs of the equine, on the rump of the equine, and any combination thereof. A sensor system or tag, or part thereof, can be attached to or integral with, for non-limiting example, a halter so that the sensor is positioned on the horse's head. Other non-limiting examples comprise sensors attached to or integral with hoof boots, horse rugs, saddles, saddle pads, fly masks, cinches, leg protectors, leg wraps, leg bandages, and any combination thereof.

A harness encircling the girth of the animal preferably comprises a padded wool girth secured to the horse with an elasticated surcingle. Preferably, the padded wool goes around the horse just behind the front legs, although it can encircle the equine anywhere on the girth.

Advantages of the wool girth include: (a) the wool girth does not rub or cause loss of hair (this is very important for trainers) and (b) elasticated surcingles are used in most yards to keep night rugs in place and will therefore be readily acceptable to trainers.

In some embodiments, in addition to the harness encircling the girth, the harness comprises at least one of: a fore-strap circling the breast of the horse, a back-strap circling the buttocks of the horse, and any combination of these.

The sensor system can be located at any position on the harness, as long as the position causes minimal interference with the movements of the equine. In the embodiment of FIG. 2A-C, where the harness encircles the girth of the equine, the sensor can be placed anywhere on the harness, as the harness is positioned such that the sensor system will cause minimal interference with the movements of the equine. Non-limiting examples of locations of the sensor system are shown in FIG. 2A-C.

FIG. 2A shows the sensor system located on the back of the equine, preferably on the withers, and preferably on or near the spine. FIG. 2B shows the sensor system located over the ribs of the equine, while FIG. 2C shows it located on the sternum or belly of the equine.

The accelerometer can be a MEMS accelerometer a piezoelectric accelerometer, a piezoresistive accelerometer, a capacitative accelerometer, a hot air bubble accelerometer, and an optical accelerometer.

The system also comprises at least one processor and at least one database. Either or both processing and database storage can be within the tag, either or both can be at a remote location, or either or both can be split between the tag and the remote location. In preferred embodiments, both processing and database storage are split between the tag and the remote location, with some of the classification of the logged activity processed in the tag and some processed at the remote location, in the external application unit.

The processor and database can comprise any processor and any database known in the art. As is known in the art, the processor and database can comprise a single unit, they can be part of the same device, or they can be comprised in different devices.

In some embodiments, processing and data storage are performed remotely; in such embodiments, the sensor system located on the equine comprises neither data processing nor data storage, except possibly for the animal ID.

In other embodiments, processing and data storage are performed within the sensor system. In these embodiments, only I/O (as described hereinbelow) is performed remotely.

In preferred embodiments, the system further comprises I/O, so that data can be entered into the processor and results output.

Input can include, but is not limited to, the name of the equine; other identifiers of the equine; date and time information; notes or comments; previous behavior of the equine; behavior of at least one other equine, either as separate files or as pooled or averaged data; and any combination thereof.

Output can include, but is not limited to, the name of the equine; other identifiers of the equine; date and time information; the frequency of rolling; the number of rolling episodes, the total amount of time spent rolling; the average length of a rolling episode; the total amount of time spent recumbent (REM sleep); the total amount of time spent lying down with the head up (non-REM sleep); the total amount of time spent eating; the total amount of time spent coughing, the number of coughing episodes, the coughing intensity; the coughing pattern; frequent wet/dry coughs; the total amount of time spent standing; the total amount of time spent moving, comprising time spent walking, trotting, ambling, pacing and galloping; a list of behavior as a function of time, which can include any behavior and any combination thereof; a pictorial representation such as, but not limited to, a graph of behavior as a function of time, which can include any behavior or combination thereof; notes; comments; warnings; and any combination thereof.

The system preferably comprises an alarm means, so that personnel can be notified of alarm conditions such as, but not limited to, colic, getting cast (stuck against a stable wall), a total lack of movement, extremely rapid pulse, extremely slow pulse, lack of pulse, a significantly raised temperature, a lowered temperature, significant or unusual sweating; unusually slow breathing, unusually rapid breathing, unusually deep breathing, unusually shallow breathing, a significantly lowered oxygen level, a significantly raised oxygen level (an identifier for abnormally rapid breathing), or a significantly raised or lowered $CO_2$ level (also indicators of abnormal breathing) and any combination thereof, for which a rapid response is needed.

In some embodiments, an alarm is triggered by the simultaneous presence of at least two of the following indicators: profuse sweating, rapid breathing (panting, >20 breaths/min), a rapid heart rate (>50 beats/min), skin that is dry and hot, an unusually high rectal temperature (>38° C.), diarrhea, slow eating, and lethargy as these are indicative of heat stress and untreated heat stress can lead to heat stroke, which can be fatal.

Another combination of symptoms that can, in some embodiments, trigger an alarm is profuse sweating followed by no sweating, especially if the profuse sweating is accompanied by one of the other indicators of heat stress as described above. The onset of complete lack of seating indicates the onset of heat stroke.

The alarm means can comprise an audible alarm such as, but not limited to, a bell or buzzer; a visual alarm such as, but not limited to, an illuminated light; a message sent to at least one person, such as, but not limited to a telephone message or an SMS; and any combination thereof.

The system preferably also comprises a warning means, so that personnel can be notified of abnormal behavior that does not require a rapid response, such as, but not limited to, unusual coughing by the equine; too little REM sleep; too much REM sleep; spending too little time eating; spending too much time eating; eating too little, eating too much, eating too fast, eating too slowly. chewing or biting on objects other than food, such as the stall or fencing; drinking too much; drinking too little; spending too little time moving; spending too much time moving, where the movement pattern is not indicative of colic; moderate sweating; rapid pulse; slow pulse, raised temperature, slightly lowered oxygen level; slightly raised oxygen level; slightly lowered $CO_2$ level; slightly raised $CO_2$ level, diarrhea, slow eating, lethargy and any combination thereof.

Stress sensors attached to the horse's skin can enable the system to determine dehydration in the equine. If the tension in the skin decreases more than a predetermined amount, the equine is becoming dehydrated and the warning means can be activated.

The motion of the animal, as detected by the sensors, is communicated to the processor and is stored in the database. From these data, behavior patterns can be determined.

Examples of normal behavior include, but are not limited to, a standing and feeding pattern, a non-REM sleep pattern (recumbent with head up), an REM (recumbent) sleep pattern, walking, trotting and galloping patterns, frisking behavior, a general movement pattern, the total amount of movement and a coughing pattern.

Other behavior patterns that can be determined include, but are not limited to, behavior during colic episodes, bucking and rearing.

In preferred embodiments, the sensor system is disposable, so that it can be replaced if any of the sensors fails. In preferred variants of systems with disposable sensor system, the sensor system is reversibly attachable to the harness, so that the sensor system can be replaced without removing the harness from the equine.

Figure 3:
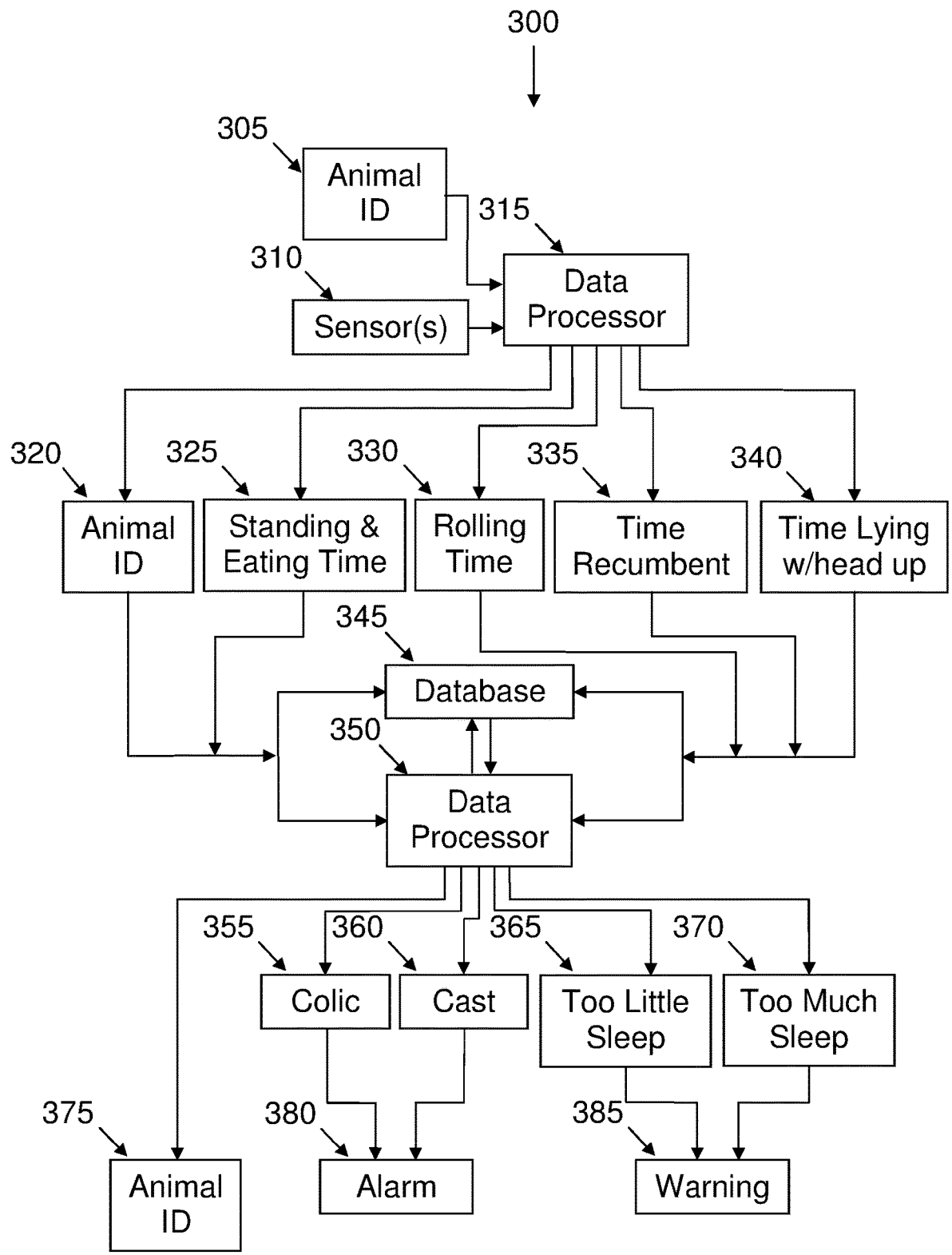
FIG. 3 depicts a block diagram on one embodiment of the functioning of the current invention.
Figure 4:
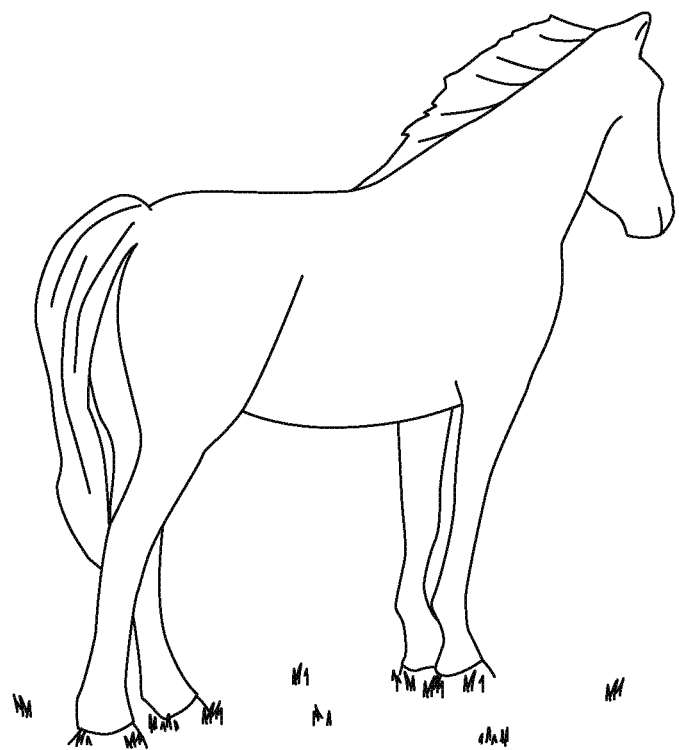
FIG. 4 depicts an equine standing.
Figure 5:
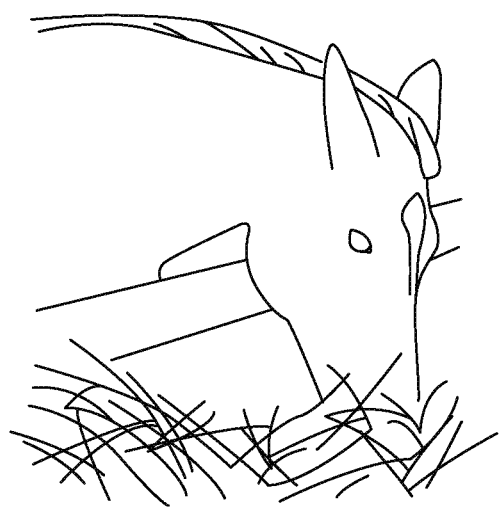
FIG. 5 depicts an equine feeding.
Figure 6:
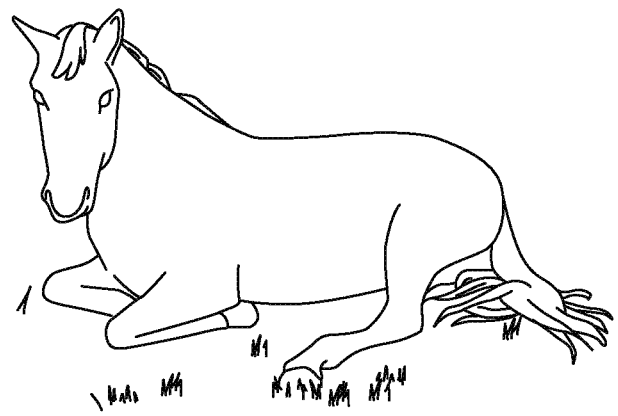
FIG. 6 depicts an equine lying with head up.
Figure 7:
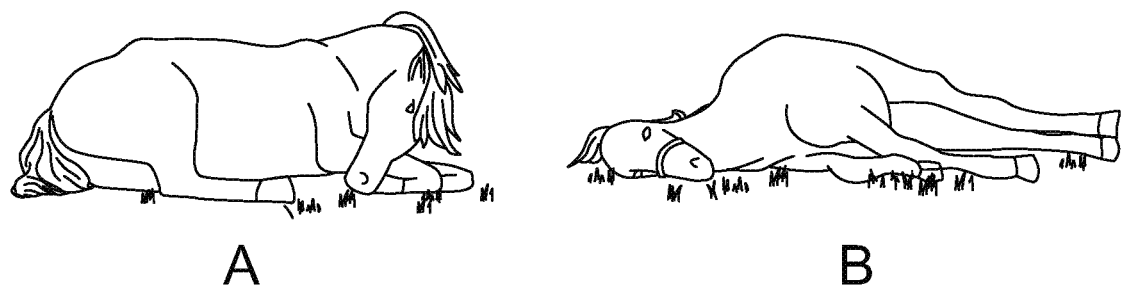
FIG. 7A-B depicts equines in REM sleep, with head down or recumbent.
Figure 8:
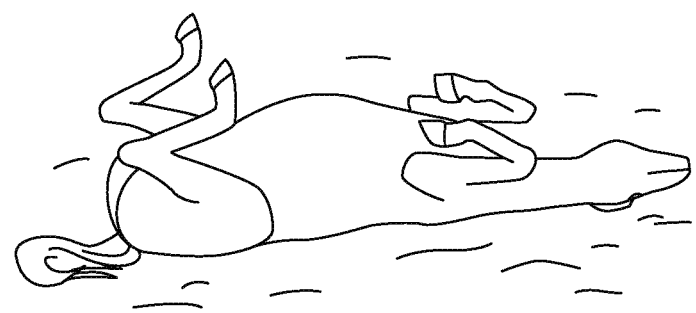
FIG. 8 depicts an equine during normal rolling.

A block diagram of an embodiment of the system is shown in FIG. 3. The system (300) comprises at least one sensor (310), which, in some embodiments, comprises a transducer for converting the detected signal to an electrical signal, a filter to reduce noise and an amplifier. The at least one sensor signal is sent to a data processor (315), as described hereinbelow. In preferred systems, each system (300) comprises an identifier (305) which uniquely identifies the equine. The identifier (305) can be stored in the data processor, stored elsewhere in the system, be comprised within a separate device in communication with the data processor (315), or any combination thereof. The data processor (315) determines, from the sensor signal or signals (310), whether the animal is standing or eating (325), rolling (330), recumbent (335), or lying with head up (340). These data (325, 330, 335, 340) as a function of time are transmitted to a database, along with the animal ID (320).

The data in the database (345), are analyzed (350) to determine, as described hereinbelow, whether the equine has colic (355), has gotten cast (360), is sleeping too little (365), or is sleeping too much (370).

If the equine has colic (365) or has gotten cast (370), immediate action is indicated, and, as described hereinbelow, an alarm (385) is activated, the alarm preferably comprising the animal ID (375).

If the equine is sleeping too little (375) or is sleeping too much (380), is spending too much or too little time eating (not shown), or exhibits an unusual coughing pattern (not shown), a warning (390) is activated, the warning preferably comprising the animal ID (375).

In some embodiments, at least one larger tag is used, preferably in conjunction with a surcingle, a saddle, a saddle pad, a horse rug, a cinch, or any combination thereof.

In some embodiments, at least one smaller tag is used. The at least one smaller tag or tags are preferably used in conjunction with a halter, a hoof boot, a fly mask, a leg protector, a leg wrap, a leg bandage, and any combination thereof, or can be placed on or attached to the equine in locations such as, but not limited to, the ear of an equine, the mane, the tail, a leg, a hoof and any combination thereof.

Use of the larger and smaller tags is not limited to the locations described above; for example, smaller tags can be used in conjunction with a surcingle, or larger tags in conjunction with a hoof boot, as long as the tag does not interfere with the movements of the animal.

Figure 9:
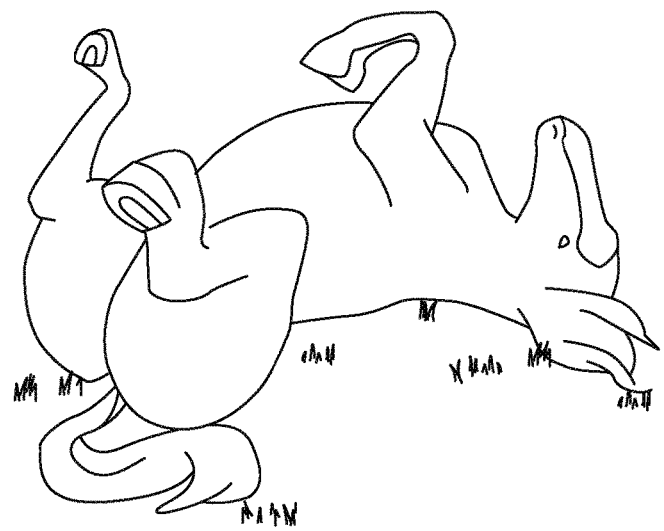
FIG. 9 depicts an equine during colic rolling.

In reference to FIGS. 4-9, equines are shown stationary (standing) (FIG. 4) and feeding (FIG. 5), lying with head up (FIG. 6), in REM sleep (FIG. 7A-B), during normal rolling (FIG. 8) and during colic rolling (FIG. 9).

Behavior patterns can be determined for a single animal or for a plurality of animals.

The behavior of a given animal can be compared to its previous behavior or to the behavior of other animals, or both.

On the basis of such comparisons, the presence of, for example, colic can be determined, either by identifying a pattern of behavior consistent with colic, or by identifying an abnormal pattern of behavior, one that does not match any known pattern of normal behavior.

In preferred embodiments, colic can be identified by erratic behavior, such as:
a) Repeated rolling and getting up—more than 3 times during a period of 15 minutes.
b) Lying down and getting up repeatedly, without rolling, more than 3 times in a period of 10 minutes.
c) Periodic rolling when a horse is lying down or recumbent if the episodes of rolling exceed 5 minutes during a 30 minute period.

In preferred embodiments, getting cast can be identified by prolonged rolling when a horse is lying down, such as more than 5 episodes of rolling during a 15 minute period.

Both too much and too little REM sleep can be indicative of problems; although the total amount of both REM sleep and non-REM sleep can vary widely between horses, if the horse experiences less than half the average amount of REM sleep or more than twice the average amount, in preferred embodiments, a warning is provided. The warning can be visual, aural, via a message, or via a display, as described above, but is preferably via a message or a display.

Other behavior patterns discernable in an equine include indicators of increased anxiety and indicators of lowered anxiety.

Indicators of increased anxiety or stress include, but are not limited to: raising of the head, a general bracing of muscles, increased respiration, widening of the eye, fixation on an object and uneven twisting of facial muscles (drawing of the nose and/or lips slightly to one side).

Indicators of lowered anxiety or stress include, but are not limited to: the lick-chew-swallow reflex, lowering the head, blinking the eyes, blowing off held breath or giving an audible sigh, licking and chewing, relaxation about the eyes and ears and muzzle, and cocking a hind leg (in a relaxed rather than threatening posture.)

It is not uncommon for horses to chew on wood, such as the wood forming its stall or loose box, the walls of the barn, or fencing or the exterior wood of buildings if the horse is outdoors. Horses can chew on wood because of missing components in the diet, such as fiber or roughage, or because of boredom. In addition, some horses seem to enjoy chewing wood; they will chew it even if they have sufficient distractors to prevent boredom and a more-than-adequate diet.

As a horse can do considerable damage to its environment by chewing on it, it can be advantageous to identify chewing of wood by the horse. Behavior patterns indicative of chewing wood include, but are not limited to, chewing with the head up or chewing with the head turned away from the manger. In some embodiments, chewing of wood is identified from the sound thereof.

A behavior related to wood chewing is "cribbing"—grabbing a board or pipe with the front teeth, arching the neck and pulling backward. In some cases, the horse will appear to suck in air when it performs this behavior. In some cases, usually referred to as "wind sucking", the horse sucks in air, but does not hold on to any object.

Other compulsive behaviors, often boredom-related or stress or anxiety-related, include head shaking, head bobbing, head tossing, head swinging, head nodding, rubbing the throat against an object, pacing, weaving, fence or box walking, stomping, tooth grinding, stall circling, striking or kicking the stall wall, pawing, digging, stall destruction, wall-climbing, rubbing the tail against an object, playing with water (sometimes including tipping over the water bucket), and general frenzied or aggressive behavior.

The animal can also exhibit repetitive tongue and lip movements, other than the normal eating and drinking tongue and lip movements. Some horses will mutilate themselves, by biting themselves, especially on the flank, chest or shoulder, or will lunge into objects.

Other behavior problem can include coprophagy or eating dirt, where the horse eats manure or dirt. This can lead to colic or gastrointestinal ulcers and other digestive disorders. In mature horses, it can be associated with a lack of roughage, protein or minerals, or with parasites.

Some horses will bolt their food instead of chewing it properly. This decreases nutrient absorption and sometimes causes choking. It can be caused by excessive hunger, a desire to finish eating before herdmates chase the horse away, competition for feed, not enough feeding space for the number of horses or failure to separate horses by size and temperament.

Repetitive behavior can have a physical cause. For example, a horse that paws or stomps its feet may have pain due to lameness or to mite infestation, which causes itchiness and irritation. Cribbing can be related to ulcers; in some cases, horses respond well to treatment of the ulcers by reducing the cribbing behavior.

Anxiety-related behavior includes, but is not limited to, restlessness, whinnying or squealing, shying, carrying the head high and tossing the tail wildly, often accompanied by flared nostrils and snorting, uncontrollable shaking or trembling, tremor in the horse's body, increased tension in the ears, head raised, usually accompanied by ears moved and held forward, and often accompanied by snorting, and pounding heart.

Stress can also lead to increased blood cortisol levels, metabolic alkalosis, inefficient transport of oxygen and energy substrates, poor tissue perfusion, thumps, muscle spasms, exertional rhabdomyolysis, cardiac arrhythmias, gastrointestinal stasis, anhydrosis, kidney impairment, and poor heart recovery from exercise-related rapid heartbeat, and poor respiratory recovery from exercise-related rapid heartbeat.

Horses kept in hot, humid conditions can develop persistently elevated blood adrenaline levels, which can lead to anhydrosis, or lack of sweating.

The motion sensor can be any sensor described in the prior art. The level of motion can be indicated by the energy of the signal. The energy level can be deduced, for example, from the RMS value of a signal produced by the sensor.

Non-limiting examples of motion sensors include:
- A glass cell holding electrodes and a drop of mercury is a known technology to measure activity. When motion exists, the mercury covers the electrodes and causes the impedance to drop.
- A metal ball that creates an electromagnetic field when changing location is also a known technology to measure activity.
- A gyroscope. MEMS motion sensors are typically gyroscopes
- A non-gyroscopic MEMS motion sensor.

Similarly, acceleration sensors can be any sensor described in the prior art. A non-limiting example of an acceleration sensor is the type based on the piezoelectric effect. However, since gravity is an acceleration, gravity affects such sensors so that the inclination of the sensor affects the reading.

The eating periods can be detected by measuring the equine's head inclination relative to the ground. When the animal eats, the equine's head tends to be lowered towards the ground, while it tends to hold its head higher when active. A sensor can measure the head inclination directly or by computing its value based on the measured output of the sensor. The sensed head inclination can be used to assess an eating status. A combination of high motion level and high values of head inclination may indicate with high probability that the animal is eating. Accumulation of an animal's sensed parameters and statistical methods can be used in order to identify eating periods.

The equine's eating periods can also be detected by monitoring and analyzing the sounds and vibrations that typically occur when an animal is eating. When an animal eats, its jaw generates sounds and vibrations that can be monitored by a sensor on the animal or inside it and then analyzed to determine an eating activity.

The animal's eating status can also be assessed by monitoring distance between its head and the ground. Small distances and high motions can indicate that the animal is eating. Measuring the distance can be done using methods outlined in prior art such as ultrasound and light.

It is possible to use a combined sensor to sense both indications of an angle of inclination of the animal's head and of motion.

Another combined sensor may be a cell partially filled with liquid and comprising a transmitter and a receiver for electromagnetic radiation, placed in two opposite sides of the cell. The transmitter may radiate electromagnetic radiation. The liquid may attenuate the radiation proportional to the amount of liquid momentarily existing between the transmitter and the receiver. The radiation may be scattered when passing out of the liquid and into the liquid, and so the radiation received by the receiver is indicative of the angle of inclination and movement of the cell. By analyzing the radiation received by the receiver a picture of accelerations and inclination along the time may be deduced.

In addition to the liquid the cell may be filled with gas or with another liquid that do not tend to mix with the first one, or with solid objects. The liquid inside the cell can be with a controllable viscosity, such as silicon, which may be suitable for the purpose of the sensor because it acts as a filter for high frequency noise.

The radiation from the transmitters doesn't have to be continuous. The transmitter can send pulses of radiation in any desirable rate, for example a few times per second for the sake of energy conservation.

Sensed information received from a sensor sensing the motion and inclination of an animal's head may comprise two distinguishable phenomena. As the head inclination is changed slowly (typically over many seconds) while the head movement is distinguishably faster, the two components of the signal received from the sensor can be separated using an analysis phase performed by a computation unit, such as a CPU, using standard digital signal processing algorithms (for example filters). The eating periods can be detected by analyzing the DC component of the received radiation signal, and the head acceleration can be detected by analyzing the AC component of the received radiation signal.

According to yet another embodiment of the present invention multiple transmitters and receivers can be used for monitoring the liquid trapped inside the cell.

According to another embodiment of the present invention one cell filled with liquid can be used for sensing motion and another sensor using different technology may be used for sensing eating related data.

According to yet another embodiment of the present invention one cell filled with liquid can be used for sensing eating related data and another sensor using different technology used for sensing motion.

According to another embodiment of the present invention, the eating status can be assessed by monitoring the distance of the head from the ground. Small distance and high motion can indicate that the animal is eating. Measuring the distance can be done using methods outlined in prior art such as ultrasound and light.

According to another embodiment of the present invention the inclination and or distance from the ground data are combined with the motion data for assessing the NUT-ACT. No explicit determination of the animal's eating state is established but rather only statistical analysis for reducing the eating periods affect is performed. Such data handling may be of larger attenuating of the motion signal as the head inclination is larger.

According to another embodiment of the present invention the animal's eating status can be determined from chewing sounds detected by a sound sensor. Data from a sound sensor can be combined with any of the motion sensing data disclosed above.

According to another embodiment, the sound sensor detects the sound of the equine coughing. Coughing can easily be distinguished from eating in that a cough typically comprises a short burst of relatively loud sound, whereas eating typically comprises a longer period of relatively continuous, relatively soft sound.

All equines cough; most are simply natural attempts to clear a transitory irritant from the respiratory tract. Normal coughing can be determined for an equine, and abnormal coughing can be identified as departures from normal coughing.

Health conditions identifiable from coughing include, but are not limited to: Frequent dry coughs unrelated to exercise can indicate a viral infection, while frequent wet coughs unrelated to exercise can indicate a bacterial infection. Wet coughing occurs when there is an accumulation of mucus in the system, while dry coughing occurs when substantially normal amounts of mucus are present. Occasional wet or dry coughs can indicate that the equine is still recovering from an earlier viral or bacterial infection. Repeated wet coughs at predictable times or predictable locations, such as in a stall, at feeding time or when being ridden can indicate chronic respiratory disease. Coughs at the beginning of exercise (but not at other times during exercise) can indicate an allergy. Coughing associated with an unusual body posture, such as standing with neck outstretched or twisted in an odd manner, or associated with retching noises, can indicate a foreign body in the airway.

Wet coughing, sometimes called "productive coughing" occurs when the cough moves mucus in the airways.

Dry coughing, sometimes called "unproductive coughing" or "non-productive coughing" occurs when the cough does not move mucus and also does not remove foreign matter from the airway.

Sound sensors can also be used to detect such sounds as the equine neighing, whinnying, squealing, snorting or otherwise vocalizing, the equine wheezing, the equine's breathing, its feet contacting the floor, its feet contacting its bedding, its feet contacting the walls of the box, its feet contacting its feeding apparatus, its head shaking (from the rattle of its halter or chain), the equine's urinating or defecating and sounds in the equine's environment. Such environmental sounds include, but are not limited to, the sounds of other equines, the sounds of other animals, mechanical sounds, weather sounds, and the sound of fire.

Non-limiting examples of the sounds of other equines include, but are not limited to, breathing, hoof sounds, neighing, whinnying, squealing, snorting or otherwise vocalizing, eating, moving, and urinating or defecating.

Other animal sounds include, but are not limited to, dogs barking, growling or yapping, cats meowing, growling or purring, other animals vocalizing, such as, but not limited to, growling, yapping, hissing, mooing, lowing, groaning, human footsteps, human speech, human whistling, human humming and human singing.

Mechanical sounds can include, but are not limited to, the sounds of heaters or air conditioners, vehicle sounds such as car, truck or tractor engines, brakes or tires or cart wheels, doors opening, including external doors and box doors, windows opening, breaking sounds such as the sound of breaking glass, tool sounds, such as drills, the sounds of hitting (hooves, axes, hatchets, fists), Weather sounds include, but are not limited to, wind, rain, and hail.

Fire sounds include, but are not limited to, crackling sounds such as are made by straw or hay burning, and popping sounds.

Sounds received by the sound sensor that activate alarm conditions can include, but are not limited to, growling, barking or yapping dogs, growling cats, other animals growling, groaning sounds, unusual hoof sounds, breaking sounds, and the sound of fires. Sounds that can activate an alarm condition if sensed at an unusual time (such as at night), can include vehicle sounds, doors opening, windows opening, human footsteps, human speech, human whistling, human humming human singing, and the sounds of drills or other tools.

Sounds received by the sound sensor that activate a warning can include, but are not limited to, growling, barking or yapping dogs, growling cats, cats meowing or purring, other animals growling, groaning sounds, unusual animal sounds, unusual hoof sounds, unusual vocalizations by other horses, strong wind sounds, loud rain sounds and loud hail sounds.

Other normal and abnormal sound patterns will be obvious to one skilled in the art.

Data on the behavior of a plurality of horses, either alone or in combination with other data, such as sound patterns, can be used to determine:

The presence of intruders, either human or other animal. Human intruders might be thieves or vandals. Animal intruders could be, for example, dogs likely to injure or frighten the horses.

Dangerous conditions, such, but not limited to, as fire, loose roofing or walls, or open doors or gates.

Unusual weather patterns likely to upset horses, such as high winds, thunder, or heavy rain.

If an abnormal condition such as the above is identified, a warning or alarm as described herein, can be provided to the trainer, an owner, the head lad, an authorized lad, a designated authorized person, or any combination thereof.

In some embodiments, the system can provide a warning or alarm, as described hereinabove, if the equine experiences colic or gets cast, especially "silent" colic or cast, which occur during the night or at other periods when no personnel are present and from which the equine has apparently recovered before the personnel appear. Such silent colic or silent cast can leave no obvious symptoms, but can, for example, cause poor performance in a racehorse.

In some embodiments, once the normal behavior of an equine is determined, the return to normal behavior after an illness or injury or an episode of colic or casting can be monitored, for example, by providing an owner or trainer with a behavior profile comprising at least one of the animal's REM sleep pattern, non-REM sleep pattern and eating pattern, thereby enabling the owner or trainer to determine when an equine is sufficiently recovered to return to full work, for example, racing or eventing.

In some embodiments, the system can monitor changes in the sleep pattern in order to assist the trainer or owner to determine whether The sleep pattern is changing as expected when an exercize routine is altered, for example, young horses may show less sleep, both REM sleep and non-REM sleep, when they enter full training.

The sleep pattern indicates the onset of an illness. Under these conditions, more sleep would be expected The sleep pattern indicates worsening or improvement in an illness The sleep pattern indicates an increase in stress, such as showing less REM sleep with, possibly, little change in non-REM sleep. An increase in general stress levels can predispose an equine to stress colic. Furthermore, increased stress can lead to worse performance, for example, on the racecourse.

In some embodiments, the system can be in communication with other systems, for non-limiting example, sources of weather data, Weatherby's, or record keeping programs, either proprietary or commercially available.

A non-limiting example of communication with Weatherby's would be, in one part of the system, checking a horse's fitness and, in another part of the system, filling in and dispatching entry forms to Weatherby's. Many other such synergies will be obvious to one skilled in the art.

EXAMPLES

Example 1

Figure 10:
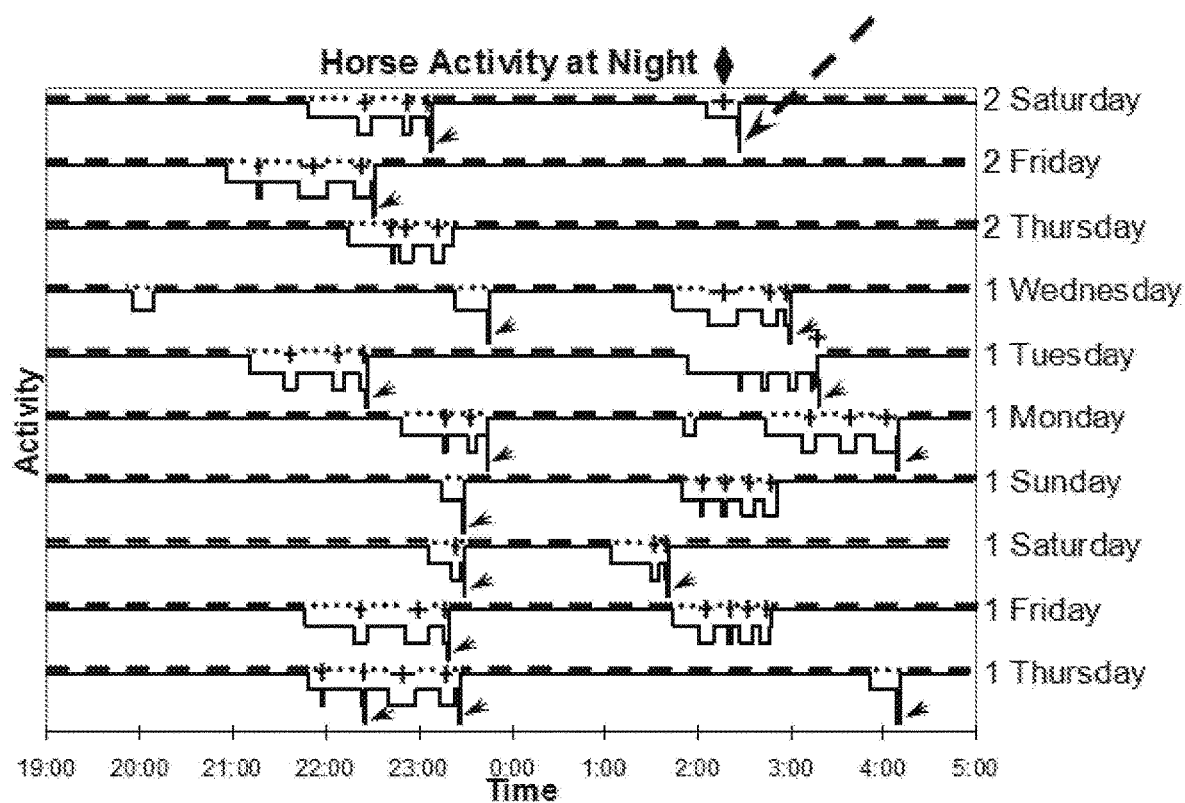
FIG. 10 illustrates the behavior of a horse during the night.

FIG. 10 shows the behavior of the horse "H" as a function of time during the night, every night over a 10 day period from the night of Thursday-Friday 21-22 February through the night of Saturday-Sunday 2-3 March. The horse was monitored from approximately 5 PM until approximately 5 AM.

For H, consistently over the 10 days, the time from about 5 PM until about 8 PM was spent feeding or moving about in the stall (dashed line). Since H was consistently feeding or moving around (dashed line) between 5 PM and 7 PM (17:00-19:00), this time period is not shown in FIG. 10.

Most nights, typically once during the night, H will have a period of "night's sleep" about 1½ to 2 hours during which he lies down with his head raised (dots), then lies recumbent (+). He then repeats this 2 or 3 times, lies with his head raised, then rolls (arrow). His "night's sleep" finished, he then stands and feeds (dashed line). On the second night he was observed (Monday of Week 1), he has two periods of "night's sleep", the first between about 22:00 and about 23:30, and the second between about 1:30 and 3:00. In the first of these, he rolls (arrow) both in the middle of the "night's sleep" and at the end of it.

This pattern is not invariable; for example, on the first Wednesday of observation, he finishes his "night's sleep" by rising from a recumbent position (+) to his feet (dashed line), without an intervening period of lying with his head up and without rolling.

He also has periods of up to about half an hour of lying with head up (dots), for example, on Wednesday of Week 1 at about 20:00 to about 20:20 and again about 23:20 to about 23:45. These periods may or may not be terminated by a roll (arrow at about 23:45).

On the last night of observation, Saturday of the second week, for the only time during the observation period, he was recumbent on the left side, the only instance of recumbency on the left side during the study. All other times he was recumbent, he lay on the right side. He terminated this period of recumbency by very energetic rolling, sufficient to turn around the collar containing the sensors (heavy dashed arrow).

It is clear that patterns of typical behavior can be derived for H from these data, and that unusual or abnormal behavior could be identified. As an example of typical behavior, H tends to have his "night's sleep" between about 21:00 and 0:00, more typically between 22:00 and 23:30, and again, or alternatively, between about 1:30 and 4:00, more typically between about 1:30 and about 3:00.

During the entire 10-day period, H never rolls from a standing position; he is either lying with head up (dots) or recumbent (+) before the roll. He usually, although not invariably, rises to his feet (dashes) after a roll, the single exception during this period being at about 22:30 on Thursday of Week 1, where he rolls from a recumbent position (+), and then assumes a position of lying with his head up (dots).

Therefore, if H were to roll from a standing position, it would probably indicate a condition such that human intervention was indicated, such as colic. This is in addition to the standard indication for colic, erratic behavior, as described above.

Examples 5-10 and 11-16 show the amount of sleep and the type of sleep for twelve racehorses, 6 from stable "A" and six from stable "B". The horses varied in age; as will be seen below, some were young horses who entered training during the period in which they were wearing their tags.

For Examples, 2-5, three horses housed in a stable yard in the UK were monitored every night for two periods, of about 2 weeks each. The horses had a work, feed and stable regime typical of horses in many parts of Europe.

Example 2

Figure 11:
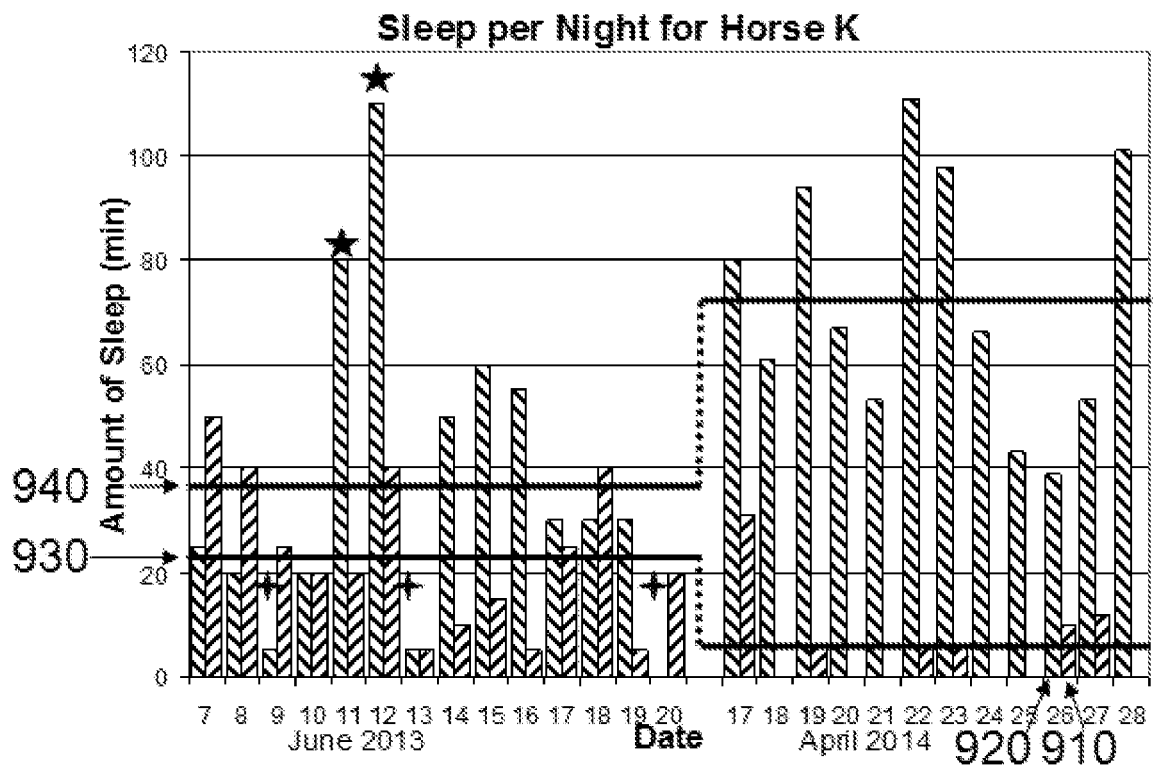
FIGS. 11-16 illustrate time spent sleeping by equines.

FIG. 11 shows the amount of sleep and the type of sleep of the horse "K" over two time periods, phase 2, the two-week period from 6 June until 20 June, and phase 3, the period from 17 April to 28 April.

K is a 15 year old gelding hunter/eventer in full work. He suffers from an incurable condition known as Cushing's. He receives 1.5 mg of Prescend medication daily, which suppresses the symptoms of Cushing's. His treatment did not change between phase 2 and phase 3.

In the two weeks of phase 2, K averaged (930) 23 minutes of non-REM sleep per night, and 40 minutes (940) of REM sleep per night, where non-REM sleep is defined as time the horse spent lying down with his head up, and REM sleep is defined as time the horse spent recumbent. The remainder of the time was spent either feeding or moving in his stall.

However, in phase 3, K's REM sleep averaged (940) 72 minutes per night, almost double what it had been in phase 2 and his average (930) non-REM sleep had decreased to 5 minutes per night although there had been no changes in his routine or work schedule. Although lethargy is one of the side effects of Prescend, such a significant increase in average (940) REM sleep in Phase 3 appeared to be a symptom of some other health problem, although his 3-mothly health check by his vet was normal. The assumption that the increase in average (940) REM sleep was indicative of further health problems appears to have been vindicated in that, after the end of Phase 3, on 7 May, K suffered a severe bout of colic and was admitted to the veterinary hospital where he received treatment for several weeks. He was successfully treated by and remains under observation.

It can be seen that the amount of both REM sleep (920) and non-REM sleep (910) varied widely, with the minimum amount of REM sleep in phase 2 being 0 minutes (on 20 June) and the maximum amount being 110 minutes (12 June); in phase 3, the minimum was 39 minutes (26 April) and the maximum was 111 minutes (22 April). In phase 2, the minimum amount of non-REM sleep was 5 minutes (13 and 19 June) and the maximum was 60 minutes (7 June), while in phase 3, the minimum amount of non-REM sleep was 0 minutes (18, 20, 21, 24, 25 and 28 April), and the maximum was 31 minutes (17 April).

On four nights, a warning was flaggable for K—on the nights of 9, 13 and 20 June (four-pointed stars), he had less than half his average amount of REM sleep; on the night of 12 June (five-pointed star) he had more than twice his average amount of REM sleep.

Example 3

Figure 12:
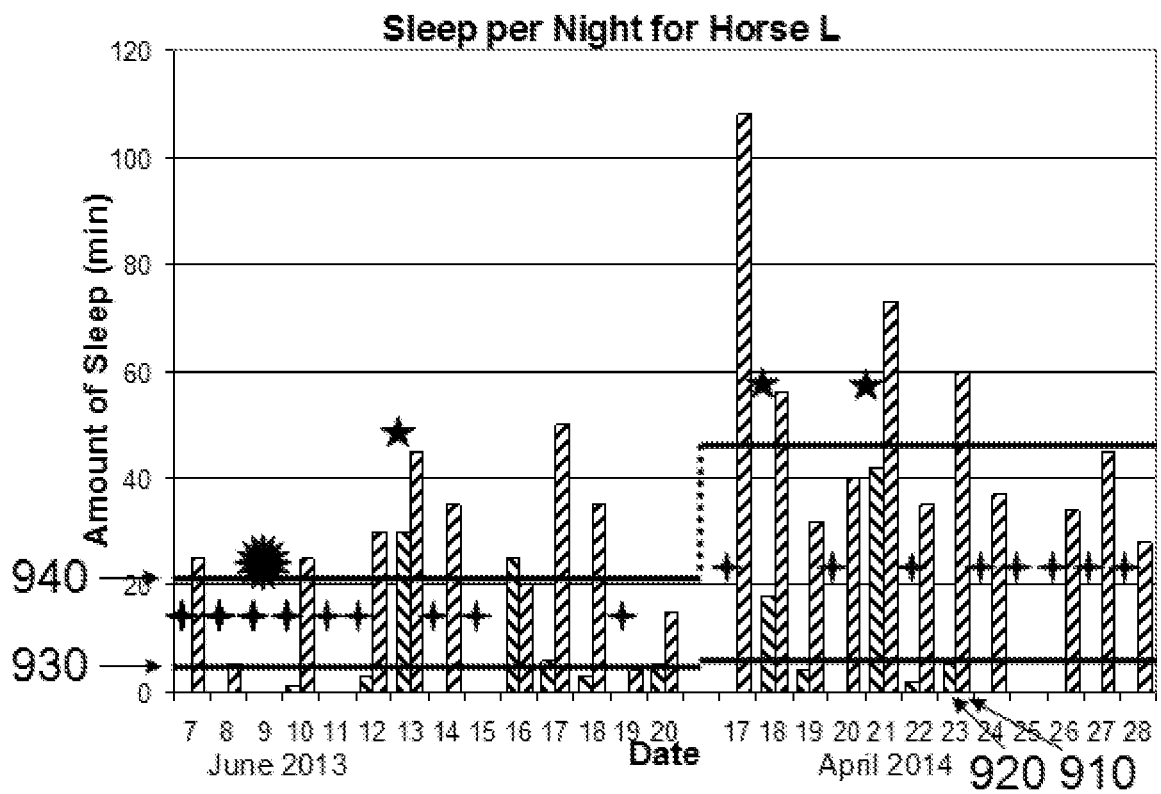

FIG. 12 shows the amount of sleep and the type of sleep of the horse "L" over two time periods, phase 2, the two-week period from 6 June until 20 June, and phase 3, the period from 17 April to 28 April.

During phase 2, she box-walked constantly. Between phase 2 and phase 3, she was moved to a new stable.

Over the two weeks of phase 2, L averaged (940) 5 minutes of REM sleep per night and 21 minutes (930) of non-REM sleep per night, where non-REM sleep is defined as time the horse spent lying down with the head up, and REM sleep is defined as time the horse spent recumbent. The remainder of the time was spent either feeding or moving in the stall.

In phase 3, L averaged (940) nearly the same amount of REM sleep, 6 minutes, but her non-REM sleep average (930) increased to 46 minutes.

It can be seen that the amount of both REM sleep (920) and non-REM sleep (910) varied widely in both phase 2 and phase 3, with the minimum amount of REM sleep being 0 minutes (on 7, 8, 9, 11, 14, 15 and 19 June in phase 2, and on 17, 20 and 24-28 April in phase 3) and the maximum amount being 30 minutes (12 June) in phase 2 and 42 minutes (21 April) in phase 3. The minimum amount of non-REM sleep was 0 minutes (9, 11 and 15 June in phase 2 and 25 April in phase 3) and the maximum was 50 minutes (17 June) in phase 2 and 108 minutes (17 April) in phase 3.

In phase 2, on 10 nights, a warning was flaggable for L—on the nights of 7, 8, 9, 10, 11, 14, 15, 16 and 19 June (four-pointed stars), she had less than half her average amount of REM sleep; on the night of 13 June (five-pointed star) she had more than twice her average amount of REM sleep.

In phase 3, on 8 nights, a warning was flaggable: on the nights of 17, 20, 22, and 24-28 April (four-pointed stars), when she had less than half her average amount of REM sleep, and on 18 and 21 April, (five-pointed star) when she had more than twice her average amount of REM sleep In phase 2, on the night of 9 June, she had an episode of colic (many-pointed star), which is clearly evident in a graph, not shown, of her behavior.

FIG. 12 indicates that L appears to be lacking sufficient sleep—she appears to be consistently getting less than the 30-60 minutes per day of REM sleep that horses appear to need.

During Phase 3, she showed no signs of box walking and her owner said she has not colicked since Phase 2 (that she is aware of). Her REM is still very low (average 6 minutes vs. 5 in phase 2) but her lying down has increased; it has doubled from 23 minutes in phase 2 to 46 minutes in phase 3.

Example 4

Figure 13:
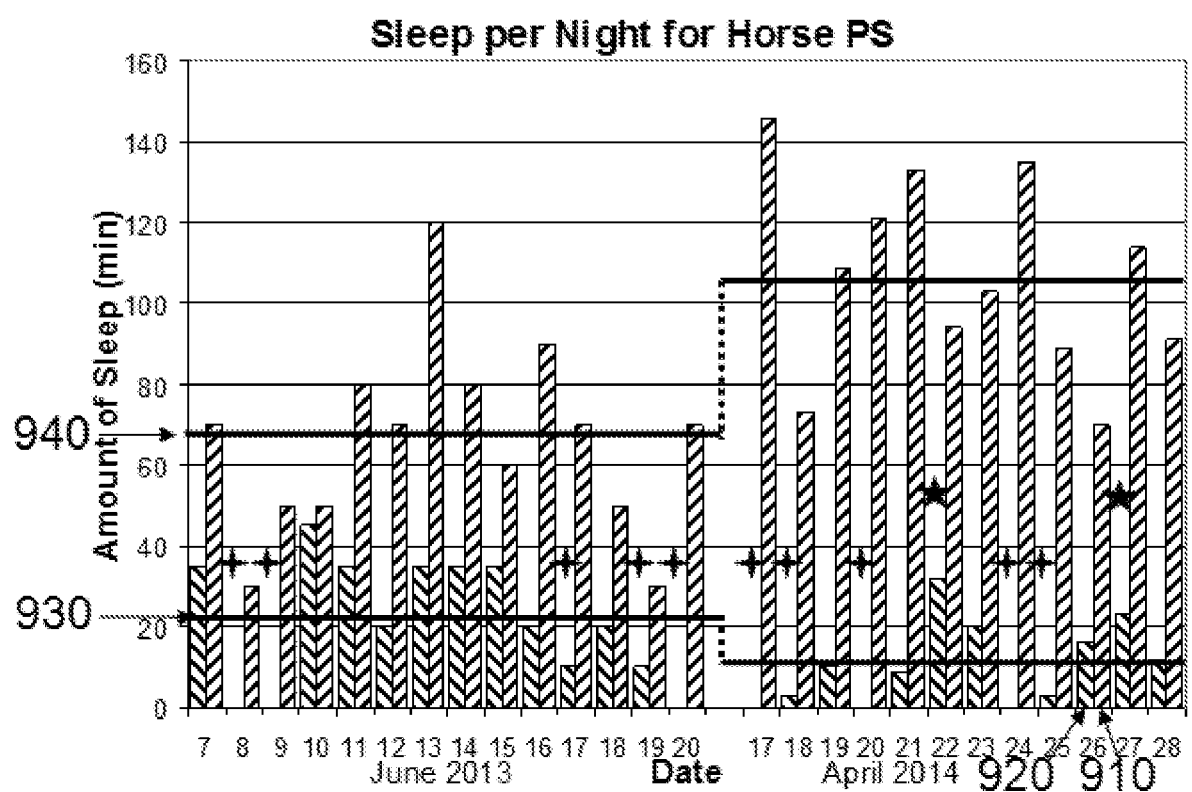

FIG. 13 shows the amount of sleep and the type of sleep of the horse "PS" over two time periods, phase 2, the two-week period from 6 June until 20 June, and phase 3, the period from 17 April to 28 April.

During the two weeks of phase 2, PS averaged (940) 22 minutes of REM sleep per night and averaged (930) 67 minutes of non-REM sleep per night, where non-REM sleep is defined as time the horse spent lying down with his head up, and REM sleep is defined as time the horse spent recumbent. The remainder of the time was spent either feeding or moving in the stall.

During phase 3, PS averaged (940) 11 minutes of REM sleep per night, and averaged (930) 107 minutes of non-REM sleep per night It can be seen that the amount of both REM sleep (920) and non-REM sleep (910) varied widely, with, in phase 2, the minimum amount of REM sleep being 0 minutes (on 8, 9, and 20 June) and the maximum amount being 45 minutes (10 June). In phase 3, the minimum amount of REM sleep (920) was 0 minutes (on 17, 20, and 24 April) and the maximum amount was 32 minutes (22 April).

The minimum amount of non-REM sleep in phase 2 was 30 minutes (8 and 18 June) and the maximum was 120 minutes (13 June), whereas the minimum amount of non-REM sleep (910) in phase 3 was 70 minutes (26 April) and the maximum amount was 146 minutes (17 April)

On 6 nights in phase 2, a warning was flaggable for PS—on the nights of 8, 9, 17, 19 and 20 June (four-pointed stars), she had less than half her average amount of REM sleep, and one one night (10 June, 5 pointed star), she had more than twice her average amount of REM sleep. Similarly, in phase 3, a warning was flaggable for PS on 7 nights—5 nights with less than half her average REM sleep (17, 18, 20, 24 and 25 April) and two with more than half her average REM sleep (22 and 27 April).

Her lying down rest increased between Phase 2 and Phase 3 but her REM significantly decreased. This may be due to her changed work routine.

It can be seen that horses' sleep patterns vary widely, both between horses and between nights for a particular horse. However, over a period of a few weeks, trends can be identified and deviations from the average can be flagged up.

Example 5

Poor Performance in a 4 Year Old Gelding Racehorse in Full Training

Figure 14A:
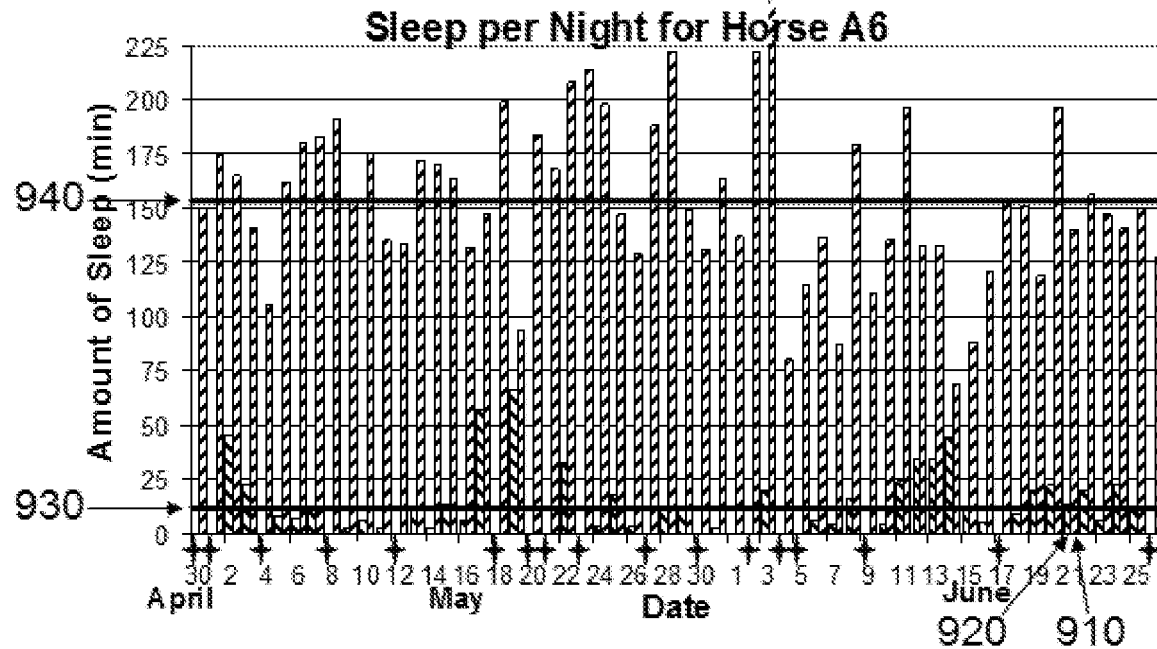
Figure 14B:
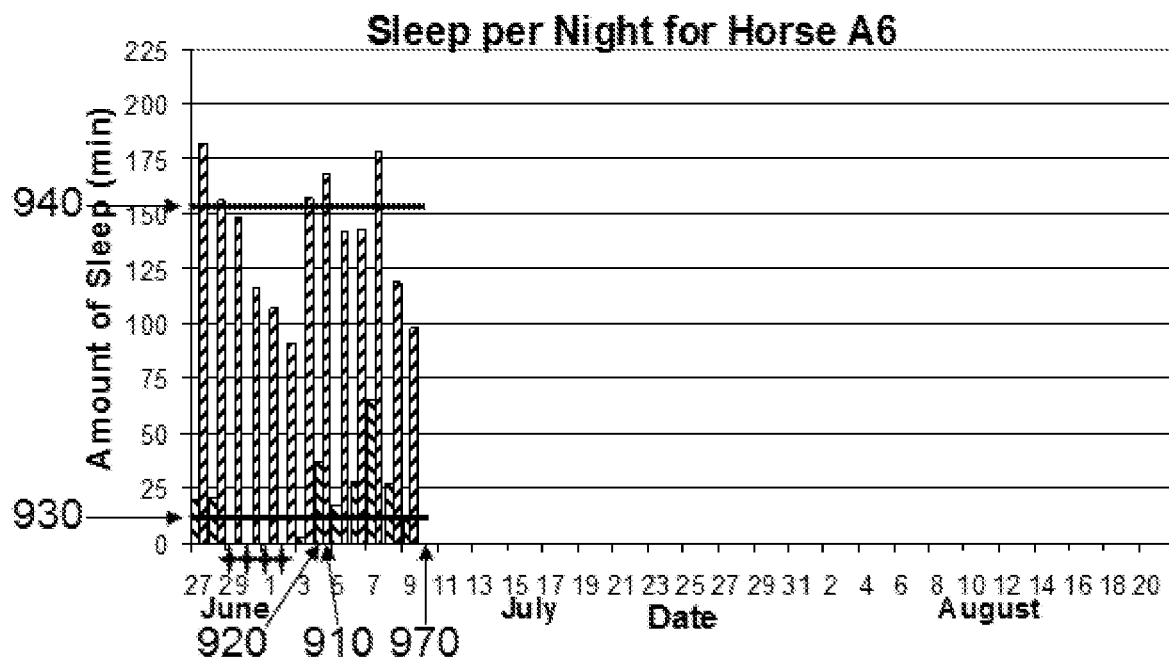

As shown in FIG. 14A-B, the horse did not have a satisfactory REM profile, averaging only about 12 minutes of sleep per night, including, on average, 2 or 3 nights a week of no REM sleep. He also spent excessive amounts of time in non-REM (lying-down) sleep (more than 150 minutes), indicating that he is suffering from severe sleep deprivation.

He began racing at 2 years old (2012). During his first racing season he had excellent form, in 2013 and in his only race in 2014 up to the end of the monitoring, he raced poorly, as shown in Table 1.

TABLE 1

| Year | 2012 | 2013 | 2014 |
|---|---|---|---|
| Result of Race | $1^{st}$, $3^{rd}$, $1^{st}$, $4^{th}$, $3^{rd}$, $3^{rd}$, $2^{nd}$ | $14^{th}$, last, last, $6^{th}$, $5^{th}$ | $6^{th}$ |

The horse appeared fit and well and had been entered in races he should have been capable of winning or at least placing (coming second or third). Instead, he has run poorly; sleep deprivation may well have been affecting his ability to perform well. It is suspected that the horse has underlying health or injury issues that have not been diagnosed despite being thoroughly examined by his vet.

On 10 July (970), the monitoring was stopped, as the horse was removed from the stables.

Example 6

Previously Undiagnosed Injury in a 6 Year Old Mare Racehorse in Full Training

Figure 15A:
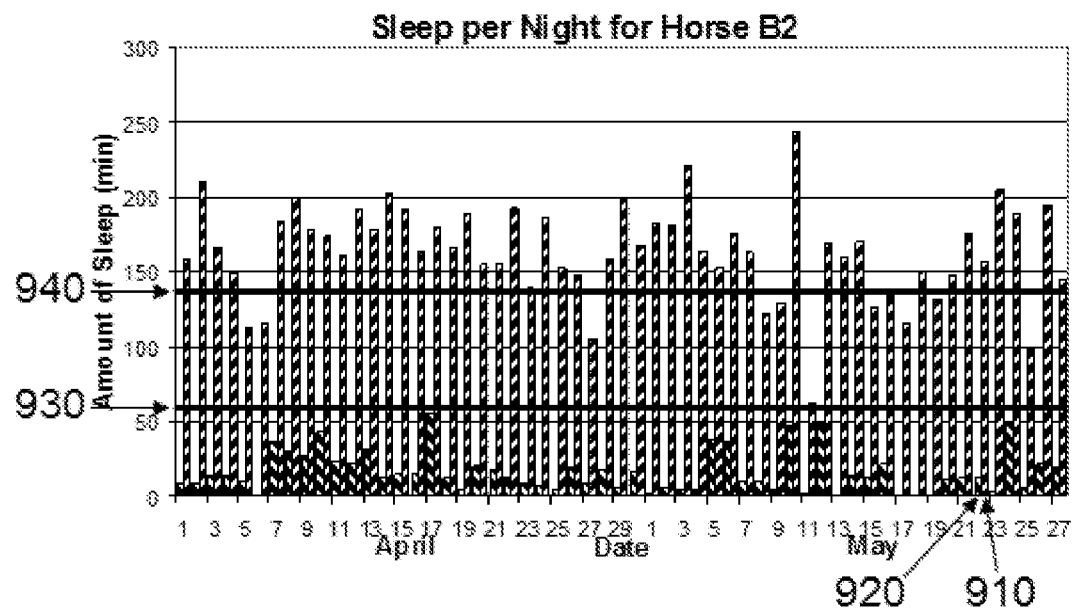
Figure 15B:
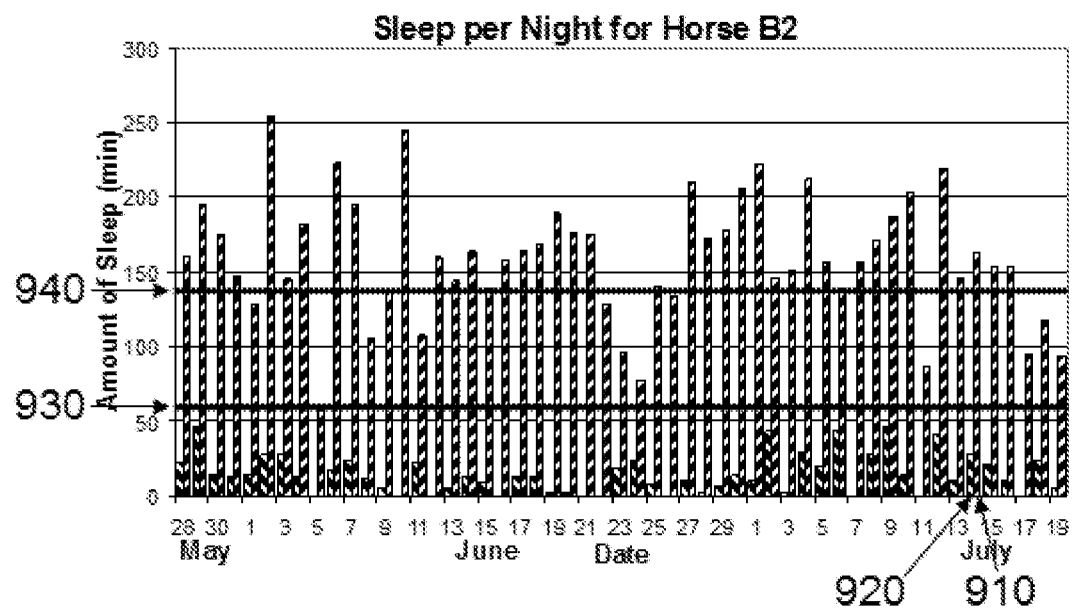

The horse, B2, appeared fit and healthy but performed badly. As shown in FIG. 15A-B, she had a very low level of REM (average 15 minutes a night) and a high level of non-REM, lying down, sleep (more than 160 minutes a night). She was also racing badly, coming in second last, second last and last in her three races in 2014, although she had won many times in previous years and had been a highly-rated horse.

A thorough examination by a veterinarian found no obvious illness or injury. A bone scan, however, revealed a fracture to the horse's left hind ankle joint and deterioration and swelling of the right hind ankle joint. Remedial treatment was carried out and the horse's work improved.

Example 7

Silent Colic in 24 Year Old Mare in Light Work and in Excellent Health

During the trial, the system detected, during the night, a bout of colic that lasted for around 4 hours. The horse showed no signs that anything was wrong preceding the colic and appeared totally normal and healthy to the owner the following morning (see FIG. 12, above).

Example 8

Silent Colic and Cast in 4 Year Old Gelding Racehorse in Full Training

Figure 16A:
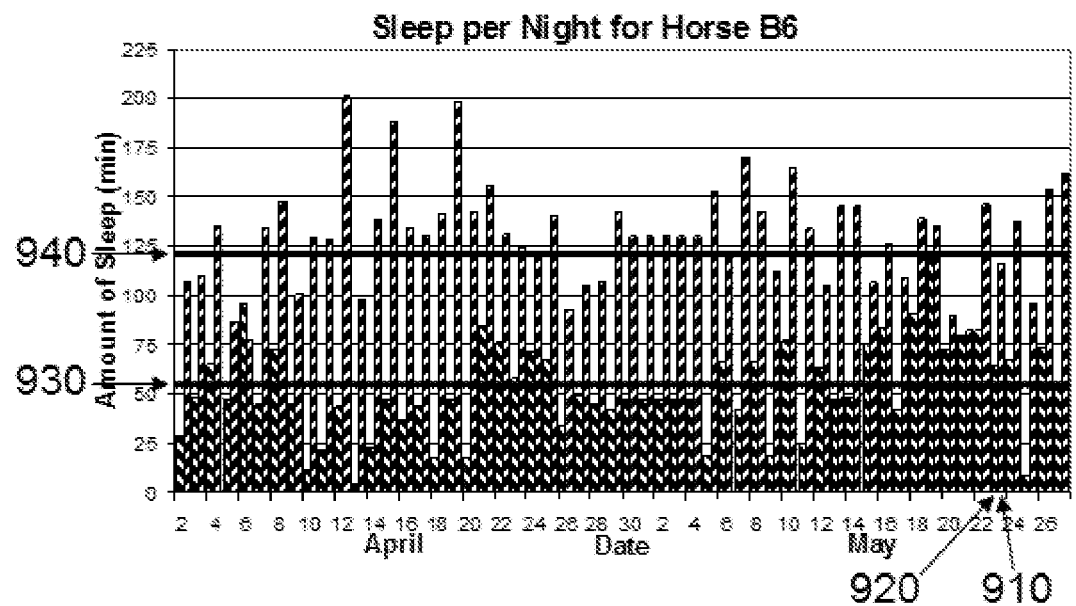
Figure 16B:
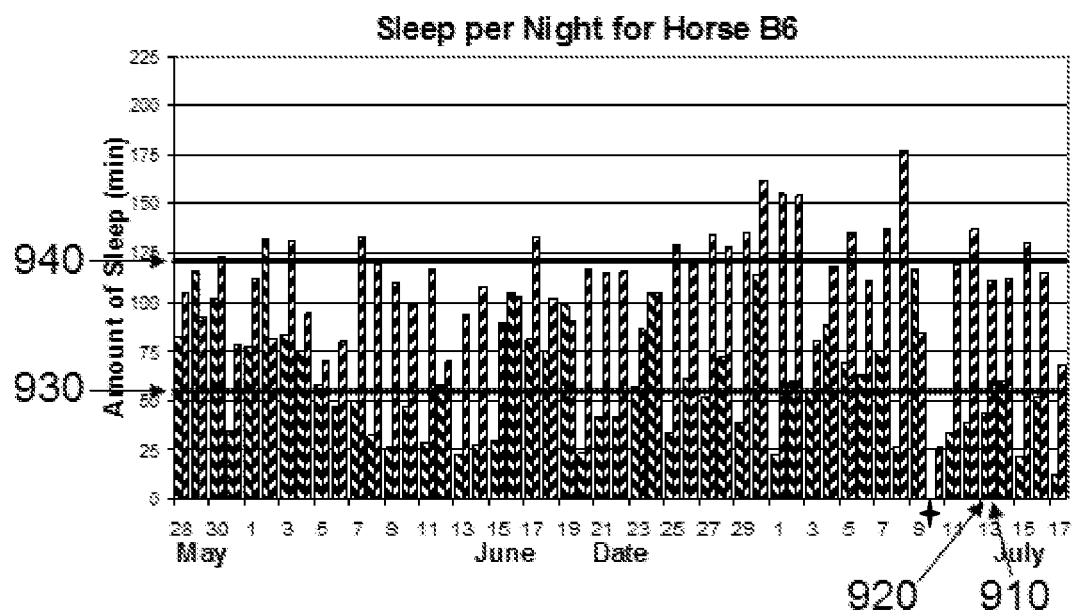

The horse, B6, had had a consistently excellent sleep profile and had run very well during the earlier part of the season (FIG. 16A-B). During the phase 3 trials, at the beginning of July, the system detected, during the night, a bout of colic followed by becoming cast (not shown). The episode lasted just under 2 hours and the horse showed no signs prior to the event and appeared fine the following morning, although, most unusually, he had no REM sleep that night (4-pointed star, FIG. 16B).

His lying down time was not significantly affected by the incident (121 min./night before the cast, 113 min/night after the cast, difference not significant), although his REM sleep time decreased significantly (55 min./night before the cast, 37 min./night afterwards). In addition, when the horse raced a few days later, he ran very poorly and continued to run poorly for the remainder of the season.

Example 9

Horse Affected by Stress of Starting Racing

Figure 17:
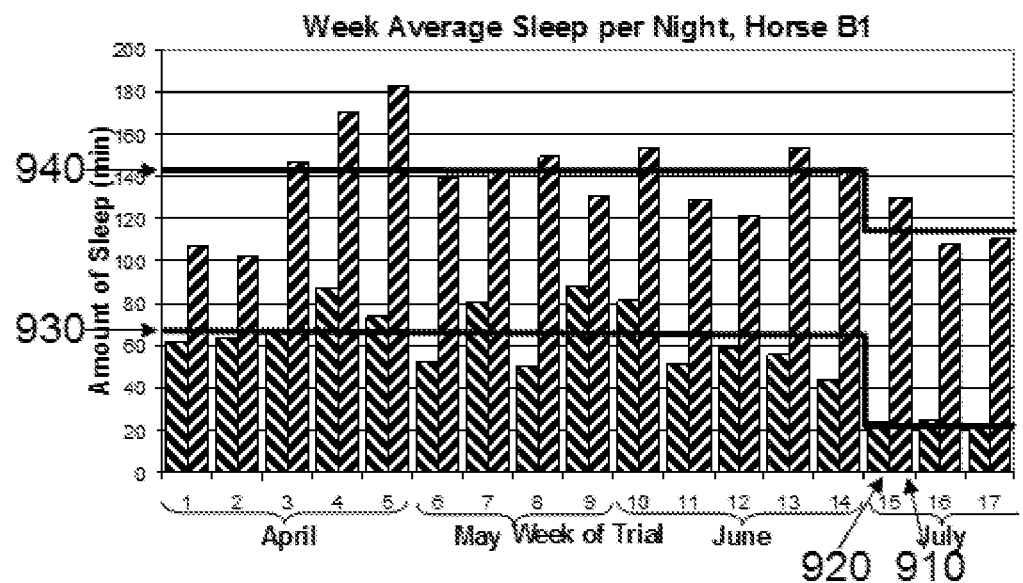
FIGS. 17-20 illustrate average time spent sleeping by equines.

During the monitoring period (FIG. 17A-B), at about Week 13-14, the horse B1 started racing (FIG. 17B). Her lying down reduced by 30% in Weeks 15-17 compared to Weeks 1-14 and her REM average reduced from 63 (Weeks 1-14) to 21 (Weeks 15-17). As there are no obvious signs of illness or injury in B1, this reduction could be due to the fact that she finds racing stressful.

Example 10

Horse Unaffected by Stress of Starting Racing

Figure 18:
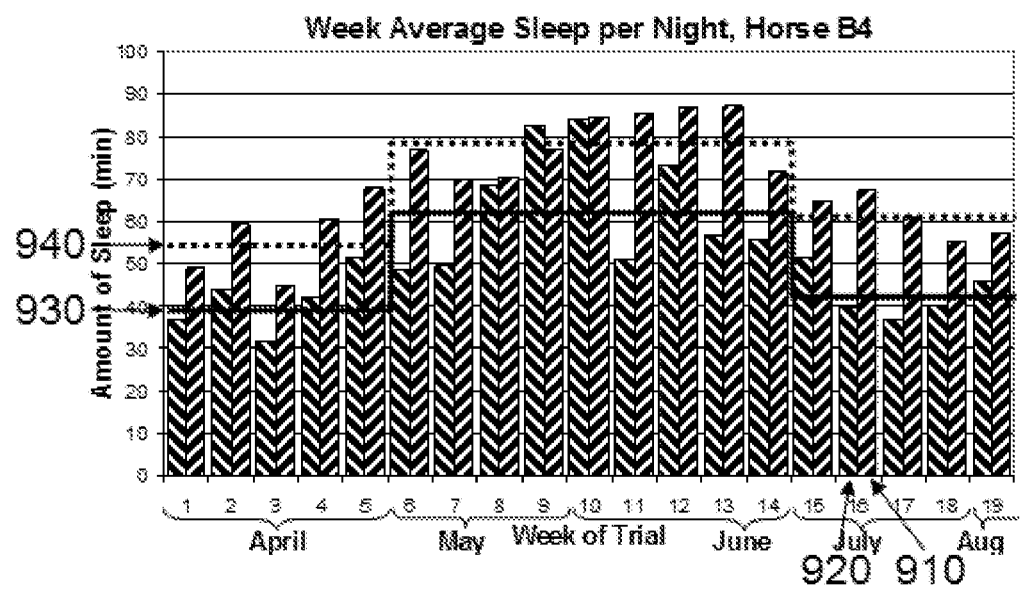

During the monitoring period (FIG. 18A-B), at about Week 13-14 (FIG. 18B), the horse B4 started racing. B4's sleep pattern falls into 3 phases during the monitoring period—weeks 1-4, characterized by less sleep overall (54 minutes lying down; 39 minutes REM), weeks 5-14, characterized by more sleep overall (78 minutes lying down; 62 minutes REM) and weeks 15-19, characterized by a return to the first pattern (61 minutes lying down; 42 minutes REM, differences not significant). The second pattern tends to be characteristic in a "bored" horse, rather than one who is ill, whereas the first pattern is more characteristic of a horse in training. It is difficult to determine from B4's sleeping pattern when he started racing this year; he is not stressed by racing, as racing has no discernable effect on his sleep pattern.

Figure 19:
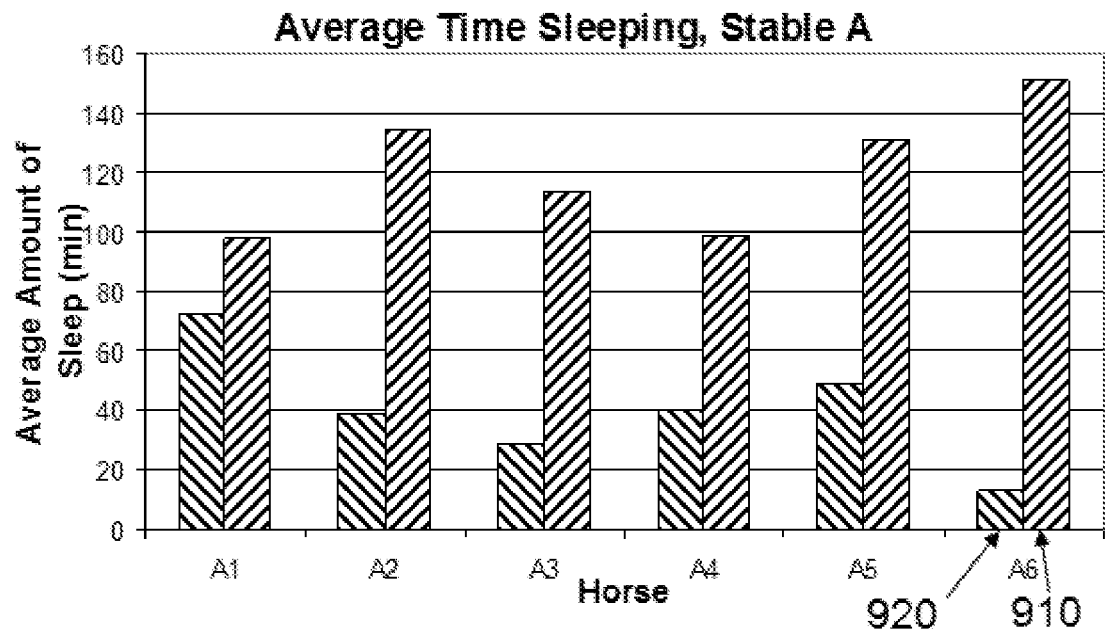
Figure 20:
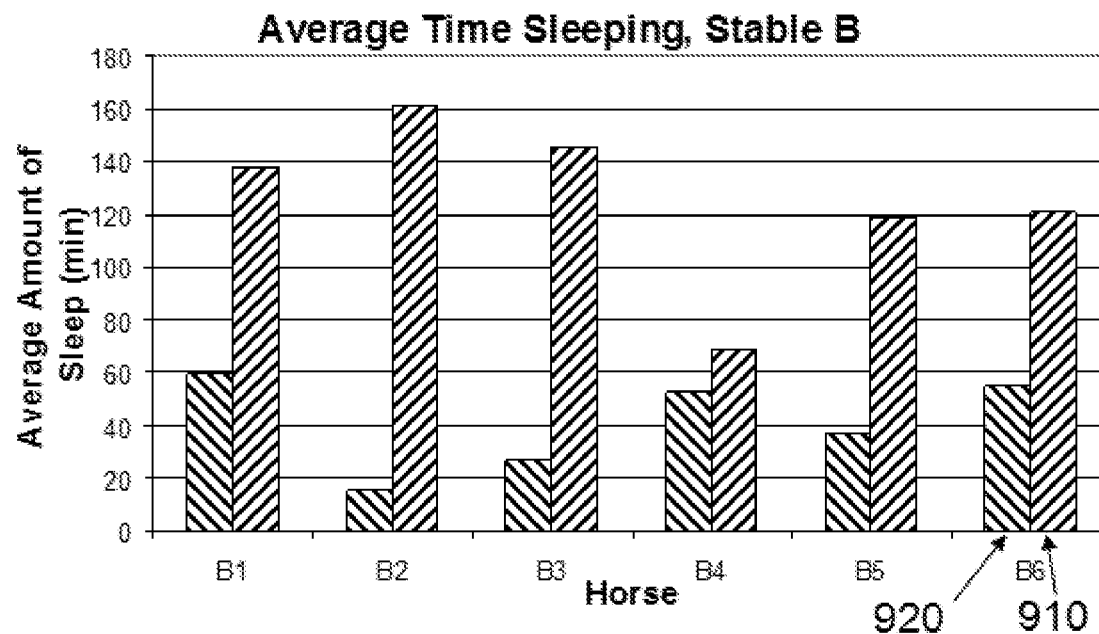

For the following examples, twelve racehorses were monitored every night for a period of about 3½ to 4 months (beginning of April to near the end of July or early August). The horses were housed in two stable yards in the UK with six horses in each stable. Some of the racehorses were training; some were young horses which entered training during the monitoring period. FIG. 19 shows the average sleep per night for the six horses in stable A and FIG. 20 shows the average sleep per night for the six horses in stable B over the period of the study. In both figures, REM sleep (920) is represented in the chart by the left bar with downward-slanting lines, while non-REM sleep (910) is represented by the right bar with upward-slanting lines.

Example 11

Referring to FIG. 19, showing the amount of sleep per night, averaged over the monitoring period, for horses in stable A. REM sleep (920) is represented on the graph by downward-slanting lines, while non-REM sleep (910) is represented with upward-slanting lines. It can be seen that all 6 horses achieved a good amount of lying down rest (910).

A3, A4 and A5 all had excellent REM profiles during the monitoring period. They had good levels of REM sleep and their sleep profiles were not only very similar to each other but also to the 4 successful horses in YARD B. These three horses, A3, A4 and A5, were also successful in races, tending to win or coming a close second or third.

Figure 21A:
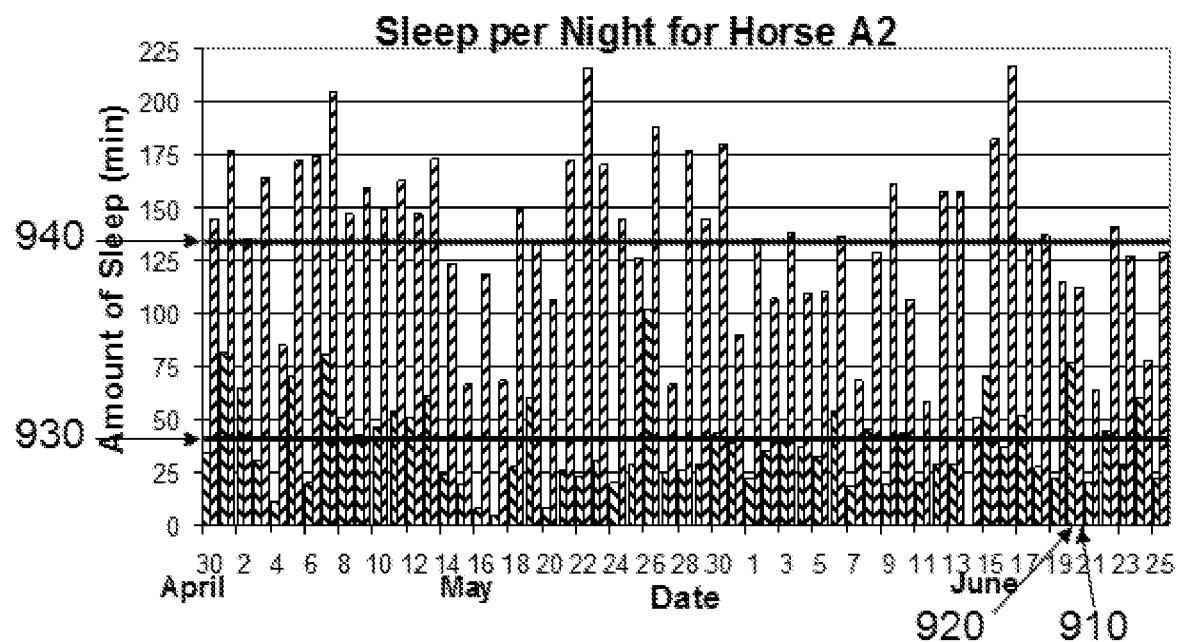
FIGS. 21-27 illustrate time spent sleeping by equines.
Figure 21B:
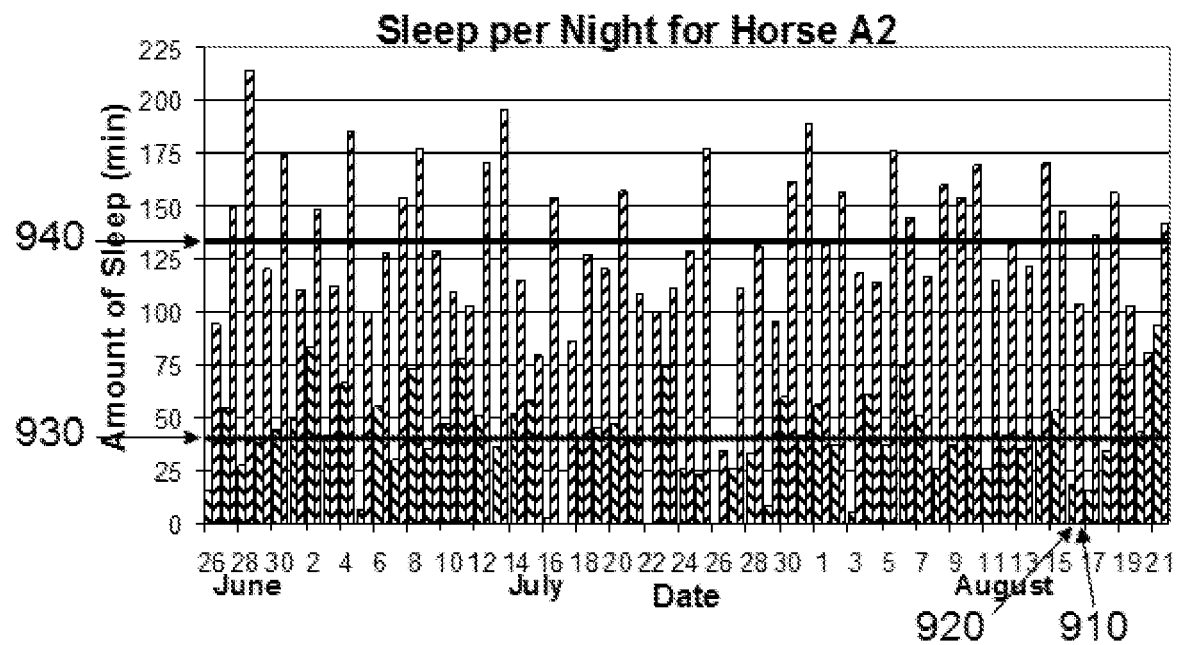

One horse, A2, is a 2 year old that has not yet raced and, like the young horse in Yard B, below, has a higher level of REM and lying down than the older horses. At the beginning of the monitoring period, A2 was more alert than the others during the night and was the only one that regularly looked over his door, which is normal for an inexperienced youngster. At the beginning of the monitoring period, he also had the highest level of REM of the six (an average of about 50 minutes per night) which, again, is usual for his age (see FIG. 21A-B). However, the amount of REM sleep decreased over the monitoring period, from the average of about 50 minutes per night to an average of about 38 minutes per night, close to the average for the other horses.

Figure 22A:
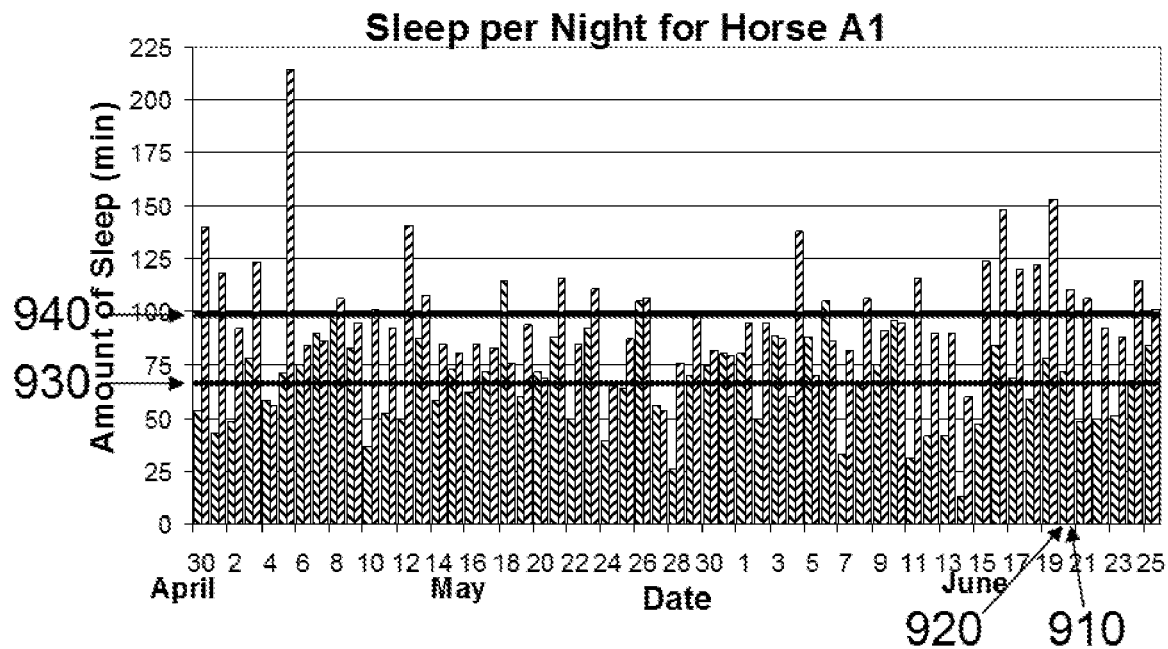
Figure 22B:
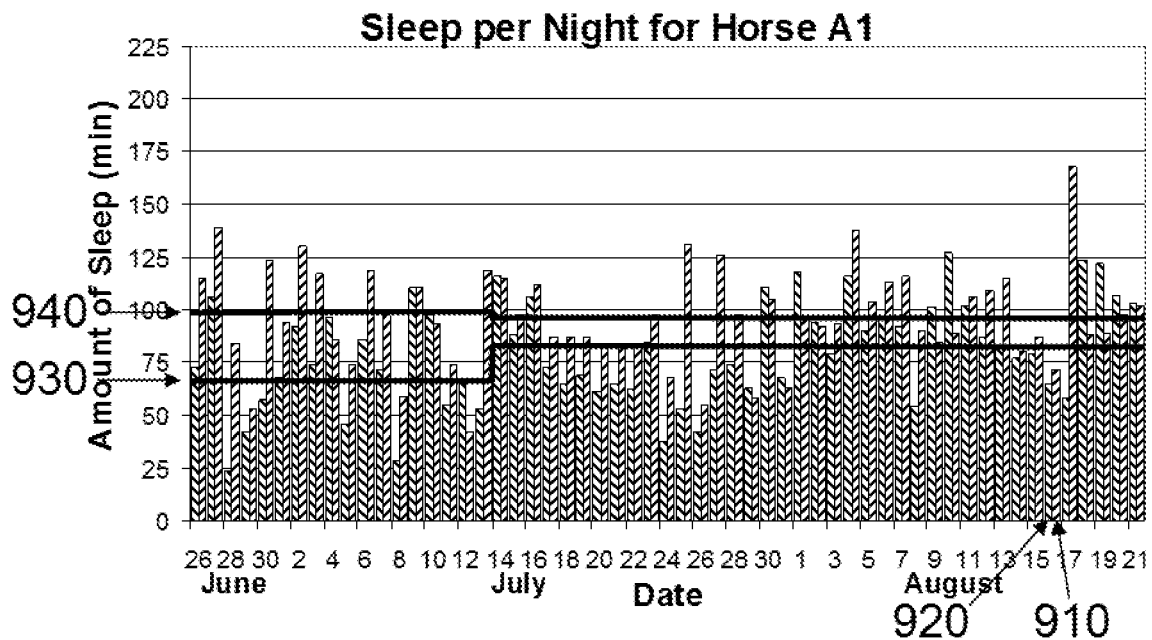

REM sleep for A1 (FIG. 22A-B) increased during the monitoring period from 48 to 69 minutes (see Example 13 below). On the night after his last race during the monitoring period, A1's sleep profile did not vary, indicating that he takes racing in his stride.

Figure 23A:
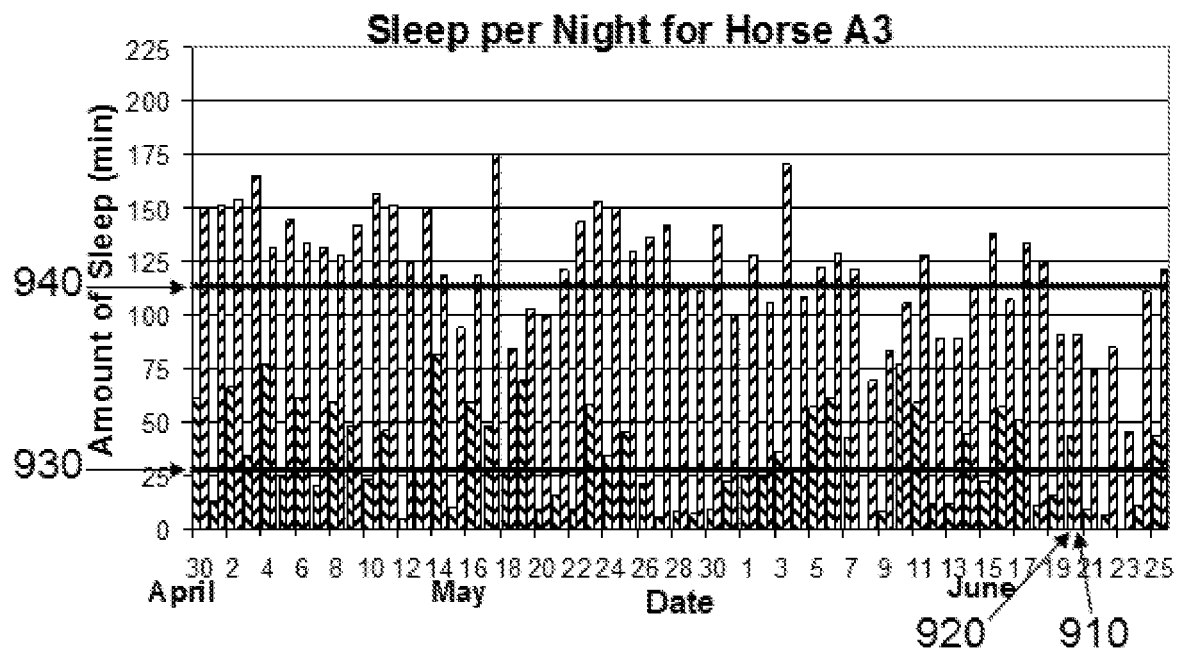
Figure 23B:
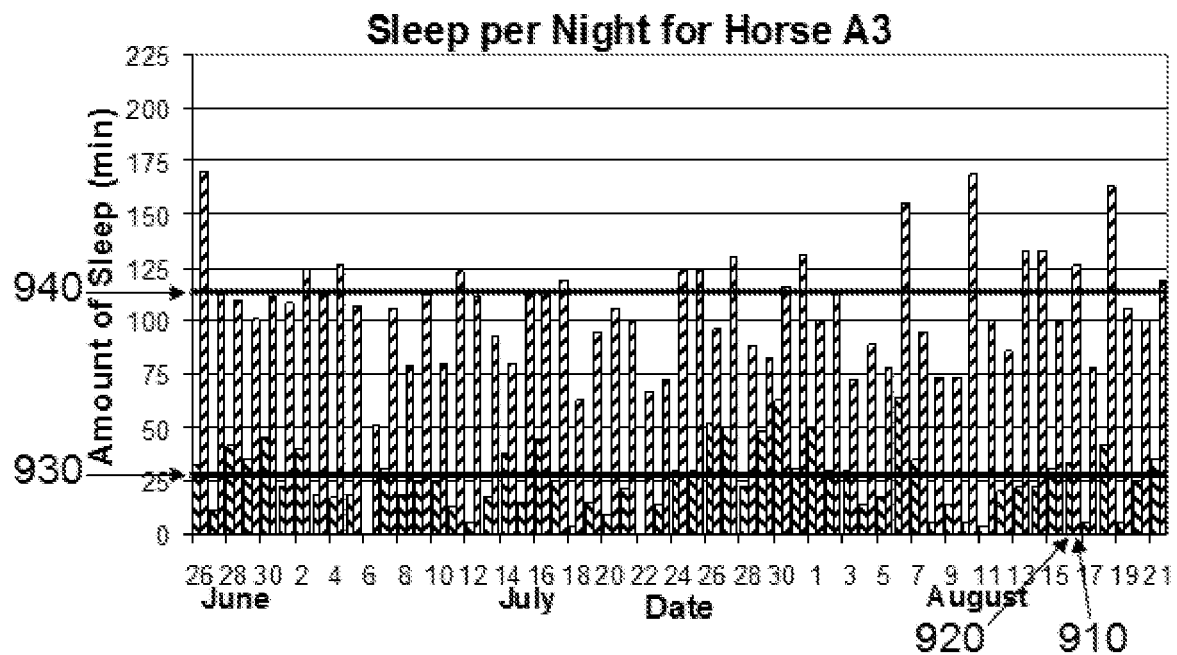

A3's sleep profile is quite inconsistent (FIG. 23A-B), with large variations in both REM (920) and non-REM sleep (910), although the average amount of REM sleep was acceptable, at 29 minutes.

Figure 24A:
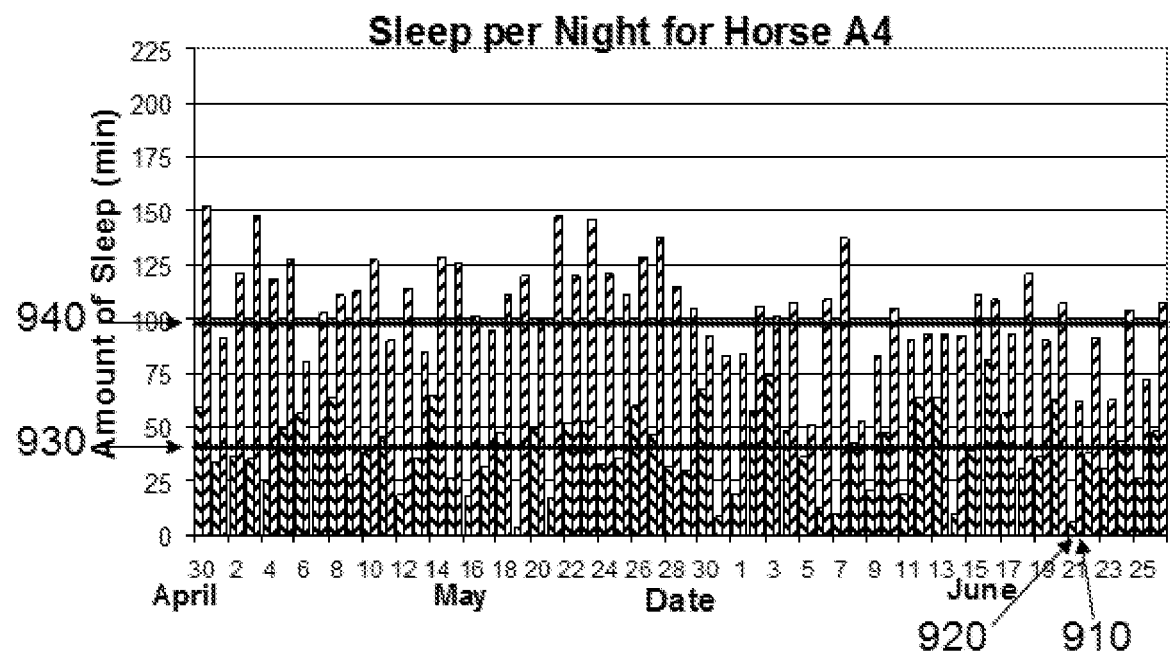
Figure 24B:
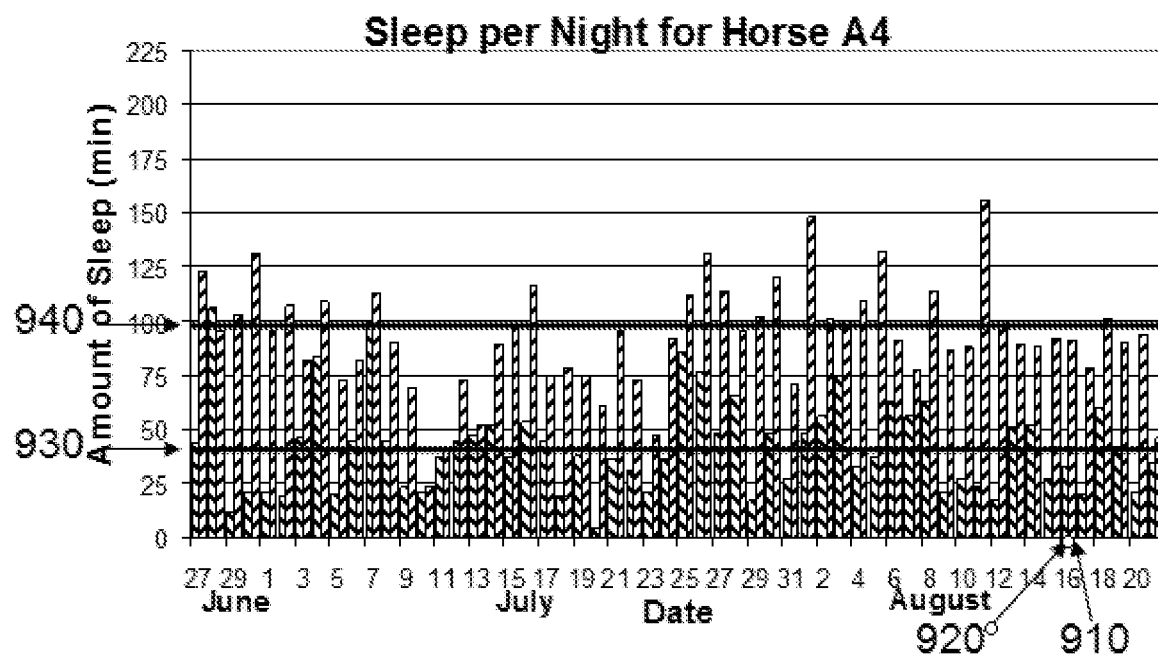

A4 has a consistently good profile (FIG. 24A-B), with an average of about 40 minutes of REM sleep during the entire monitoring period.

A5 (FIG. 16A-B) had a very good sleep pattern (not shown) for much of the monitoring period, with REM of 49 minutes, and no variation on nights he raced.

One horse, A6, a 4 year old, discussed in Example 5 (FIG. 14A-B), above, did not have a satisfactory REM profile, averaging only about 11 minutes of sleep per night, including, on average, 2 or 3 nights a week of no REM sleep (see FIG. 14A-B). He also spent excessive amounts of time in non-REM (lying-down) sleep (more than 150 minutes), indicating that he is suffering from severe sleep deprivation.

Example 12

FIG. 20 shows the average sleep per night over the 1½ months of the study for the six horses in stable B. REM sleep (920) is represented on the graph by downward-slanting lines, while non-REM sleep (910) is represented with upward-slanting lines.

All 6 horses achieved a good amount of lying down rest (910).

Three, B3, B4 and B5, had excellent current racing results either winning or coming a close second or third. They had a good level of REM sleep and their sleep profiles were very similar to each other and to the four successful horses from Stable A.

B1, who had her first race during the monitoring period, had, during the earlier phase of monitoring, the highest level of REM sleep (66 minutes, later decreasing to 59 minutes, more than 10 minutes a night more than the 53 minutes of B4) which is usual for a healthy young horse, particularly if she is in a growing phase.

During the monitoring period, the amount of REM sleep by B4 increased by an average of 10 minutes per night (from 42 mins to 53 mins). He also became very consistent, with the amount of REM sleep almost unchanged after the last race during the monitoring period.

B5 has a rock solid profile with excellent REM (average 37 minutes). The night after a race, he increases his rest time and achieves no REM sleep, but the following night he is back to his normal average in both REM and non-REM sleep.

Figure 25A:
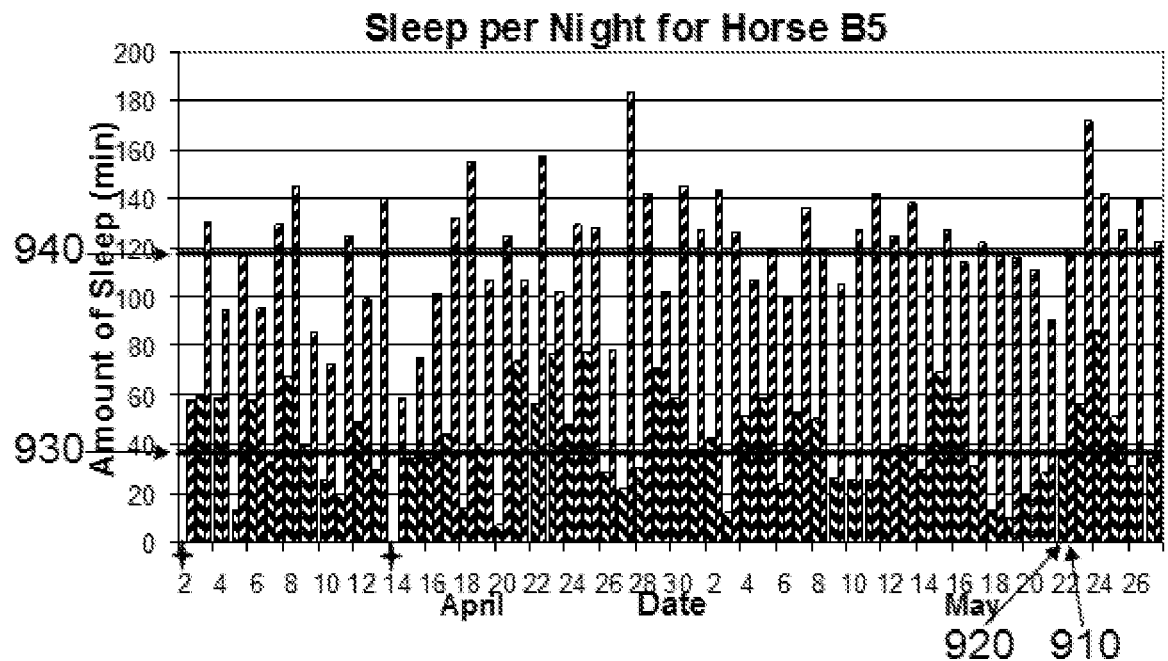
Figure 25B:
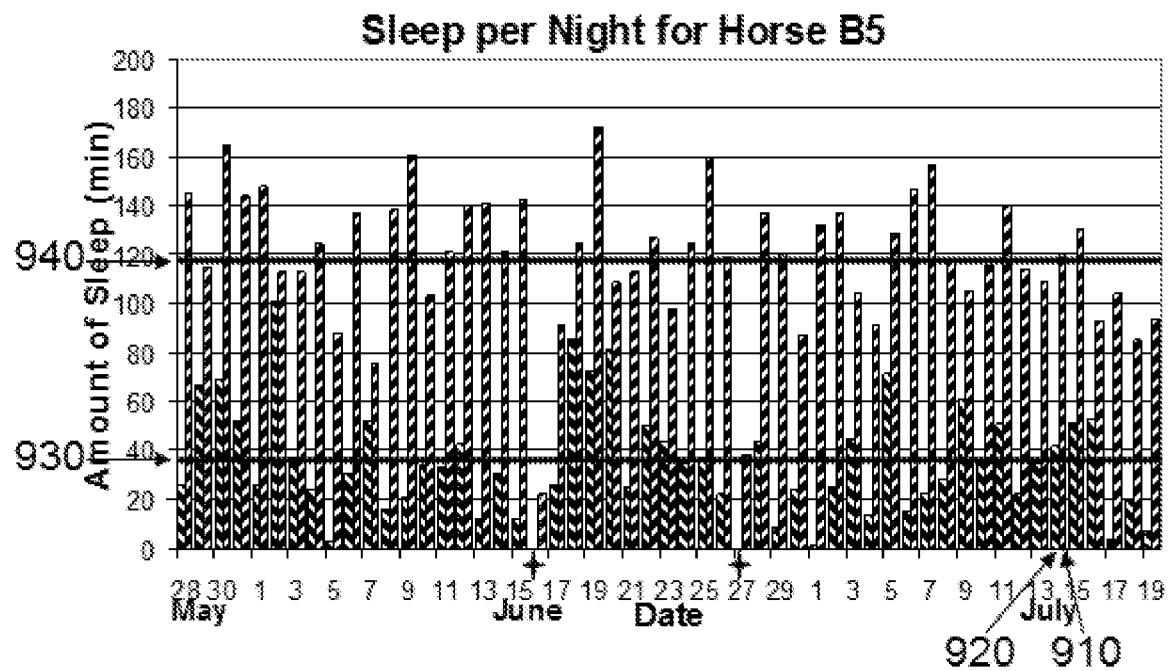

B5 (FIG. 25A-B) has a nearly ideal sleep and rest profile for a racehorse—average REM sleep about 40 minutes a night, average non-REM sleep (910) (lying down resting) about 120 minutes per night, night-to-night consistency and little variation in sleep pattern after a race.

Figure 26A:
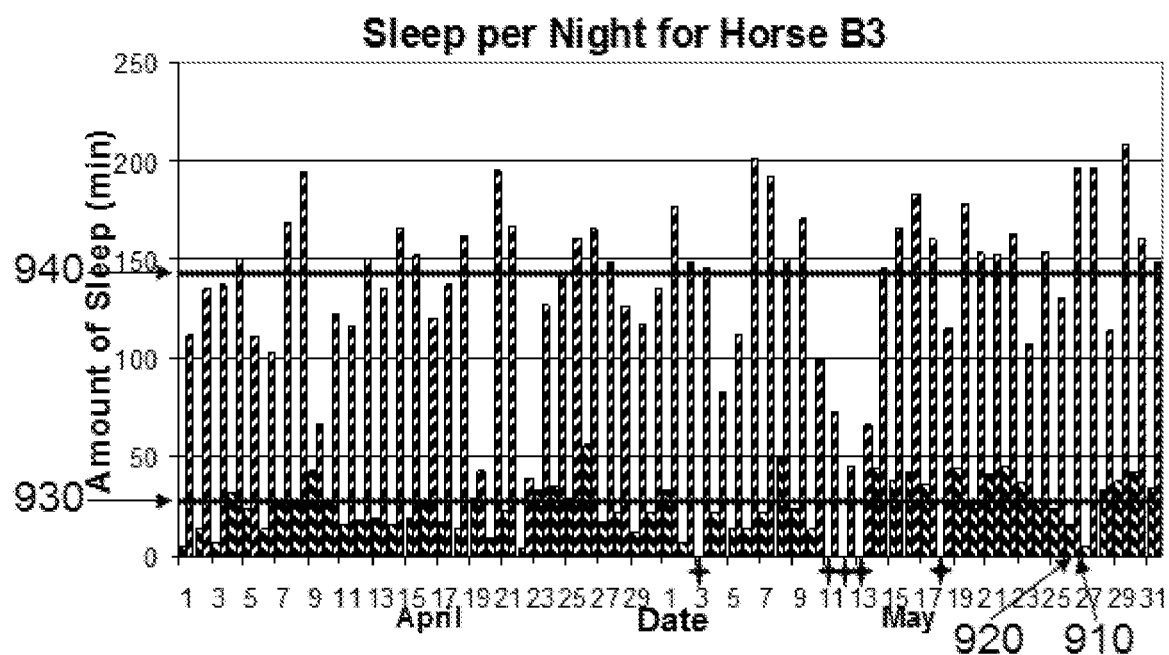
Figure 26B:
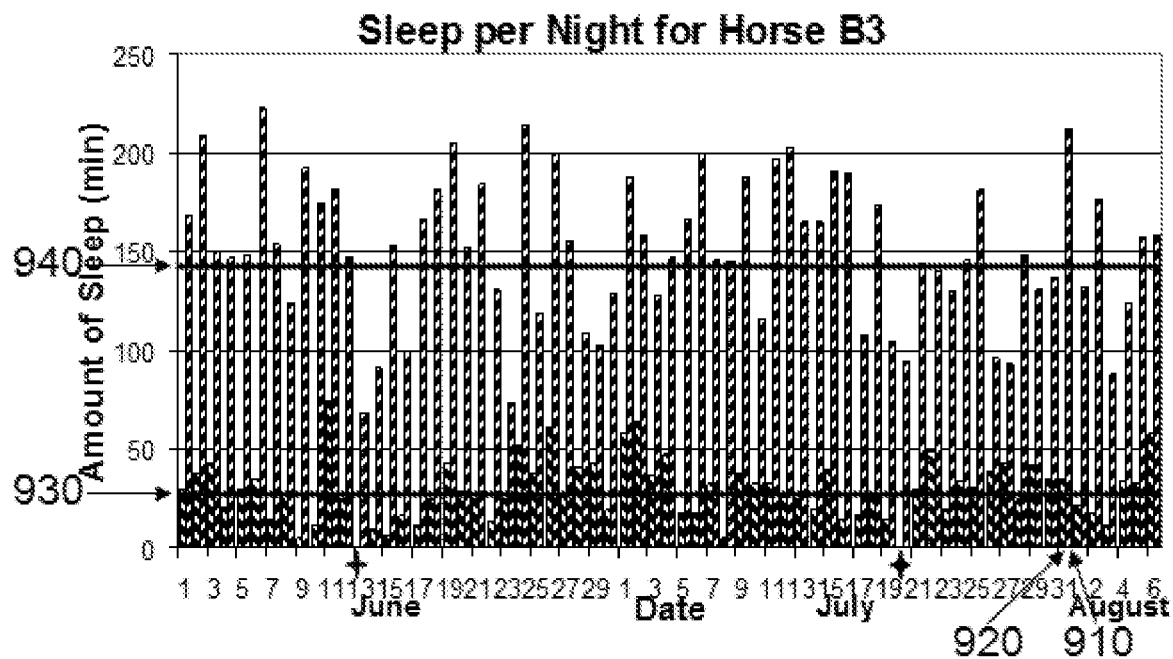

B3 (FIG. 26A-B) also has a low REM, but the data indicate that this is probably not due to unwellness or stress in the horse. The night after a race—and on other random nights, possibly after a piece of work he finds hard—he has no REM sleep (4-pointed star). Some of the other horses also show no REM sleep after a hard workout, such as a race, but it is more typical for a horse to exceed its average, often by up to 100%, after missing a night's sleep, then gradually drop back to their normal level of REM sleep. B3 does not; he skips a night's sleep and then returns straight away to his normal low average. As he appears fit and well also appears to run well—winning a race during the monitoring period—it can be assumed that this somewhat atypical sleep profile works for this horse.

B2, like A6 from stable A, was suffering from sleep deprivation, as she combined a very low level of REM sleep (average 15 minutes a night) with a high level of non-REM sleep (more than 160 minutes a night), indicating that there was probably something wrong with her. She was also racing badly, coming in second last, second last and last in her three races in 2014, although she had won many times in previous years and had been a highly-rated horse. Further investigation found that she had a fractured left hind ankle joint (see Example 6, and FIG. 15A-B, above).

B6 (see Example 8 and FIG. 16A-B) had a good profile for much of the monitoring period, until he suffered a silent colic and cast, after which his sleep pattern deteriorated.

Example 13

From 1 April to 14 July of the monitoring period 1 April to 20 August, the horse A1 had an excellent REM profile, with about 99 min. of non-REM sleep and about 67 minutes of REM sleep. However, in the latter part of the monitoring period, from about 15 July to 20 August, although the non-REM sleep changed by only an insignificant amount (97 min.), the REM sleep increased significantly, to 84 min.

Figure 27:
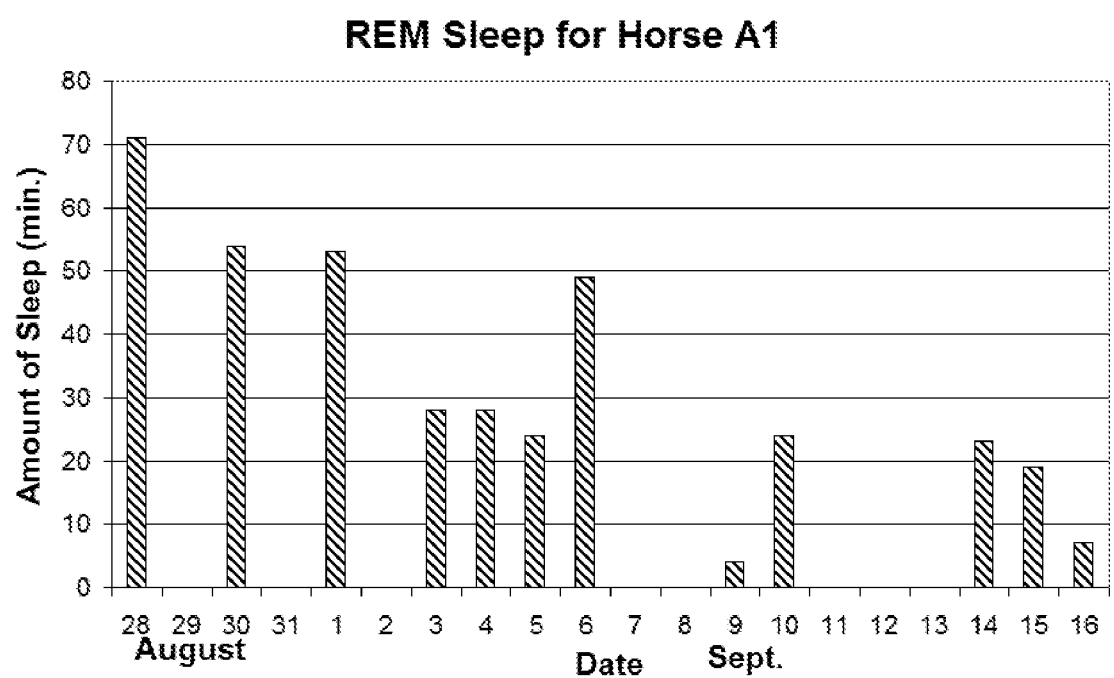

Blood tests were done, which diagnosed a respiratory infection. After a course of antibiotics, the horses' REM profile returned to about its previous norm. However, the amount of REM sleep continued to drop (FIG. 27) and the horse was sent to a veterinary clinic between 11 and 13 September, where a bone scan revealed a fracture to his left foreleg.

This clearly demonstrates the connection between sleep profile variations and ill health or injury. Neither the virus nor the fracture was discernible, prior to veterinary diagnosis, from symptoms, other than the abnormal sleep pattern, displayed by the horse.

From the above examples, from the sleep pattern alone, the following can be determined:
1. Performance horses that are successful in their races have similar sleep profiles.
2. Performance horses with low levels of REM perform badly in their races.
3. Young horses need higher levels of rest and REM than older horses.
4. Significant increase in REM can indicate illness or worsening of an existing medical condition.
5. Low levels of REM in a performance horse can indicate that the horse is suffering from an undiagnosed illness or injury.

If, in addition, the horse's rolling behaviour is monitored, the following can be determined:
1. "Silent" cast.
2. "Silent" colic.

Either sound patterns or group behaviour of the horses can indicate the following:
1. Human intruders.
2. Non-human intruders.
3. Abnormal weather patterns (thunder and lightning, high wind, etc.)
4. Fire.

In addition, as can be seen from the above, the system of the present invention can be used to determine when a horse is fit to return to full work, such as, but not limited to, eventing or racing after an illness or injury. As shown above, the sleep pattern is a sensitive indicator of wellness in an equine and an equine that appears to be well but retains an abnormal sleep pattern is unlikely to do well in a demanding situation such as, but not limited to, racing. Therefore, if a horse recovering from an injury or from illness is eating well and exercising well but still shows an abnormal sleep pattern, the owner or trainer would be well-advised not to return the horse to full work until the sleep pattern returns to normal.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A system for behavioral monitoring for equines, comprising:
   a. at least one first sensor, comprising at least one first wireless transmitter; said at least one first sensor is configured to sense motion of at least a portion of said equine;
   b. at least one database in communication with said at least one first wireless transmitter, said at least one database configured to store at least one parameter of said equine as a function of time;
   c. processing means in communication with said at least one database, said processing means configured to (i) determine, from at least one signal from said at least one first sensor, said at least one parameter of said equine as a function of time; (ii) establish normal behavior of said equine based on said at least one parameter of said equine as a function of time; and (iii) identify at least one abnormal behavior of said equine by identifying at least one deviation from said normal behavior; and,
   d. a warning mechanism in communication with said processing means, said warning mechanism is selected from a group consisting of an audible alarm, a visual alarm, a message sent to at least one person, and any combination thereof;

said abnormal behavior being selected from two or more behaviors of colic, getting cast, undiagnosed injury, not getting sufficient REM sleep, getting too much REM sleep, and any combination thereof
   wherein
   at least one of said at least one first sensor is positioned on the body of said equine;
   colic is identifiable by a behavior selected from a group consisting of repeated rolling and getting up, lying down and getting up repeatedly without rolling, periodic rolling, and any combination thereof; repeated rolling and getting up consisting of rolling and getting up more than 3 times during a period of 15 minutes; lying down and getting up repeatedly without rolling consisting of lying down and getting up without rolling more than 3 times in a period of 10 minutes; and periodic rolling consisting of rolling from a lying down or recumbent position with the episodes of rolling exceeding approximately 5 minutes during an approximately 30 minute period;
   getting cast is identifiable by prolonged rolling, there being more than 5 episodes of rolling during a 15 minute period, the equine rolling from a position selected from a group consisting of lying down with head up and recumbent and,
   undiagnosed illness or injury is identifiable by an abnormal sleep pattern.

2. The system of claim 1, wherein said at least one parameter is selected from a group consisting of position of at least a portion of said equine, movement of at least a portion of said equine, sound pattern made by said equine, temperature of said equine, pulse rate of said equine, movement of said equine, oxygen level of said equine, $CO_2$ level of said equine, sweating of said equine, sound pattern in said equine's environment and any combination thereof; said at least one position of said equine is selected from a group consisting of (a) equine standing and feeding; (b) equine lying down with head up; (c) equine recumbent; (d) equine rolling, (e) equine rearing, (f) equine bucking, and (g) any combination thereof; said sound pattern made by said equine is selected from a group consisting of: eating pattern, coughing pattern, neighing pattern, whinnying pattern, squealing pattern, snorting pattern, sighing pattern, other vocalizing patterns, wheezing pattern, pattern of hoof sounds from contact with the floor, pattern of hoof sounds from contact with the equine's bedding, pattern of hoof sounds from contact with the walls of the box, pattern of hoof sounds from contact with feeding apparatus, pattern of head shaking, urinating pattern, defecating pattern and any combination thereof; said coughing pattern is selected from a group consisting of: the frequency of coughing, the duration of individual coughs, the duration of a series of coughs, the loudness of coughs, coughing comprising wet coughs, coughing comprising dry coughs, the time of day of the coughing, the movement pattern of the equine at the time of the coughing, and any combination thereof; said sound pattern in said equine's environment is selected from a group consisting of: breathing, hoof sounds, neighing, whinnying, squealing, snorting, sighing, otherwise vocalizing, eating, moving, urinating, defecating, non-equine animal vocalizing, footsteps, human speech, human whistling, human humming, human singing, mechanical sounds, weather sounds, and any combination thereof; said non-equine animal vocalizing is selected from a group consisting of: barking, growling, yapping, meowing, purring, hissing, mooing, lowing, groaning, and any combination thereof.

3. The system of claim 2, wherein, from said at least one parameter, is determinable a pattern of abnormal equine condition selected from a group consisting of: abnormal sweating, temperature too high, temperature too low, oxygen level too high, oxygen level too low, $CO_2$ level too low, $CO_2$ level too high, rearing, bucking, moving too much, moving too little, eating too much, eating too little, eating too fast, eating too slowly, chewing objects other than food, biting objects other than food, chewing without eating, drinking too much, drinking too little, drinking too fast, drinking too slowly, uttering an abnormal coughing pattern, an abnormal sound pattern in said equine's environment and any combination thereof; said abnormal coughing pattern of said equine is selected from a group consisting of: coughing too often, coughing too seldom, individual coughs of too short duration, individual coughs of too long duration, too short a series of coughs, too long a series of coughs, overly loud coughs, overly quiet coughs, wet coughing, persistent dry coughing, coughing at an unusual time of day, increased coughing at a particular time of day, coughing during exercise, coughing in the stable, coughing in the aftermath of exercise, coughing in the lead-up to exercise, coughing during prolonged exercise, coughing in the aftermath of prolonged exercise, coughing during prolonged exercise, coughing in the aftermath of prolonged exercise, coughing while stabled, coughing while in the pasture, wheezing and any combination thereof; said abnormal sound pattern in said equine's environment is selected from a group consisting of: hooves hitting the floor too much, hooves hitting the floor too little, hooves hitting the bedding too much, hooves hitting the bedding too little, hooves hitting walls too much, hooves hitting objects too much, hooves hitting objects too little, and any combination thereof.

4. The system of claim 2, wherein said equine's health status is obtainable from said abnormal coughing pattern of said equine; said abnormal coughing pattern is indicative of at least one selected from a group consisting of a viral infection, a bacterial infection, recovering from a bacterial infection, chronic respiratory disease, allergic reaction, accumulation of mucus, a foreign object lodged in the airway, and any combination thereof.

5. The system of claim 1, wherein said abnormal behavior indicates change in said equine's anxiety status, said change in said equine's anxiety status is selected from a group consisting of raised anxiety and lowered anxiety, said indicator of raised anxiety is selected from a group consisting of: raising of the head, a general bracing of muscles, increased respiration, widening of the eye, fixation on an object, uneven twisting of facial muscles and any combination thereof and said indicator of lowered anxiety is selected from a group consisting of: the lick-chew-swallow reflex, lowering the head, blinking the eyes, blowing off held breath or giving an audible sigh, licking and chewing, relaxation about the eyes and ears and muzzle, cocking a hind leg in a relaxed rather than threatening posture, and any combination thereof.

6. The system of claim 1, wherein said sensor comprises a member of a group consisting of: an accelerometer, a motion sensor, a sound sensor, an oxygen sensor, a $CO_2$ sensor, a pressure sensor, a velocity sensor, a temperature sensor, a moisture sensor, a stress sensor and any combination thereof.

7. The system of claim 1, further comprising a member of a group consisting of: an ID, said ID uniquely identifying said equine; a harness, at least one second sensor in communication with said equine, and any combination thereof;
(a) said harness selected from a group consisting of: an elasticated surcingle configured to encircle the girth of said equine, a halter on said equine's head, a hoof boot, a horse rug, a saddle pad, a saddle, a fly mask, a cinch, a leg protector, a leg wrap, a leg bandage, and any combination thereof; said member of said sensing group is either permanently or reversibly attachable to said harness;
(b) said second sensor being in communication with said at least one database via at least one second wireless transmitter; said at least one database configured to store at least one environment parameter selected from a group consisting of: a parameter of said equine's environment, a parameter of said equine's environment as a function of time, and any combination thereof; said first sensor and said second sensor either separate or integrated together; said at least one first wireless transmitter and said at least one second wireless transmitter either separate or integrated together; said processing means are further configured to establish, from said at least one environment parameter from said at least one second sensor, a member of a group consisting of a normal environment of said equine, and a normal environment of said equine as a function of time, an abnormal environment of said equine identifiable from a member of a group consisting of: any deviation from said normal environment, and any said time-related deviation from said normal environment; and a trigger for said abnormal behavior is identifiable as said deviation from said normal environment or said time-related deviation from said normal environment;
(c) said warning mechanism is in wireless or wired communication with said processing means; said warning mechanism additionally configured to provide notification of said abnormal environment; said audible alarm is selected from a group consisting of: a constant-pitch sound, a variable-pitch sound, a constant-volume sound, a ringing sound, a buzzing sound, a voice message, a variable-volume sound, and any combination thereof; said visual alarm is selected from a group consisting of: an illuminated light, a visible picture, a constant-color light, a variable-color light, a constant-brightness, a variable-brightness light, and any combination thereof; and said message is selected from a group consisting of an audible telephone message, an SMS message, a message displayed on a display and any combination thereof.

8. The system of claim 1, wherein a member of a sensing group consisting of said at least one first sensor, said at least one second sensor and any combination thereof is locatable at a place selected from a group consisting of: the girth of the equine, the head of the equine, the neck of the equine, the withers of the equine, a leg of said equine, a rump of said equine, and any combination thereof.

9. A method for monitoring behavior of equines, comprising steps of:
a. providing a system for behavioral monitoring for equines, comprising:
  i. at least one first sensor comprising at least one first wireless transmitter; said at least one first sensor is configured to sense motion of at least a portion of said equine;
  ii. at least one database in communication with said at least one first wireless transmitter, said at least one database configured to store at least one parameter of said equine as a function of time;
  iii. processing means in communication with said at least one database, said processing means configured to (1) determine, from at least one signal from said at least one first sensor, said at least one parameter of said equine as a function of time; (2) establish normal behavior of said equine based on said at least one parameter of said equine as a function of time; and (3) identify at least one abnormal behavior of said equine by identifying at least one deviation from said normal behavior; and,
  iv. a warning mechanism in communication with said processing means, said warning mechanism is selected from a group consisting of an audible alarm, a visual alarm, a message sent to at least one person, and any combination thereof;
b. positioning said at least one first sensor in communication with said equine;
c. determining said at least one parameter of said equine from said at least one first sensor's signal;
d. storing said at least one parameter of said equine in said at least one database as a function of time;
e. establishing said normal behavior of said equine; and
f. identifying said deviation from said normal behavior, thereby identifying said abnormal behavior;
said abnormal behavior being selected from two or more behaviors of colic, getting cast, undiagnosed injury, not getting sufficient REM sleep, getting too much REM sleep, and any combination thereof
wherein at least one of said at least one first sensor is positioned on the body of said equine; thereby
  identifying colic by a behavior selected from a group consisting of repeated rolling and getting up, lying down and getting up repeatedly without rolling, periodic rolling, and any combination thereof; repeated rolling and getting up consisting of rolling and getting up more than 3 times during a period of 15 minutes; lying down and getting up repeatedly without rolling consisting of lying down and getting up without rolling more than 3 times in a period of 10 minutes; and periodic rolling consisting of rolling from a lying down or recumbent position with the episodes of rolling exceeding approximately 5 minutes during an approximately 30 minute period;

identifying getting cast by prolonged rolling, there being more than 5 episodes of rolling during a 15 minute period, the equine rolling from a position selected from a group consisting of lying down with head up and recumbent; and, identifying undiagnosed illness is identifiable by an abnormal sleep pattern;

additionally comprising a step of said warning mechanism providing a warning if said abnormal behavior is identified.

10. The method of claim 9, additionally comprising steps of: selecting said at least one parameter from a group consisting of position of at least a portion of said equine, movement of at least a portion of said equine, sound pattern made by said equine, temperature of said equine, pulse rate of said equine, movement of said equine, oxygen level of said equine, $CO_2$ level of said equine, sweating of said equine, sound pattern in said equine's environment and any combination thereof; (a) selecting said at least one position of said equine from a group consisting of equine standing and feeding; equine lying down with head up; equine recumbent; equine rolling, equine rearing, equine bucking, and any combination thereof; (b) selecting said sound pattern made by said equine from a group consisting of: eating pattern, coughing pattern, neighing pattern, whinnying pattern, squealing pattern, snorting pattern, sighing pattern, other vocalizing patterns, wheezing pattern, pattern of hoof sounds from contact with the floor, pattern of hoof sounds from contact with the equine's bedding, pattern of hoof sounds from contact with the walls of the box, pattern of hoof sounds from contact with feeding apparatus, pattern of head shaking, urinating pattern, defecating pattern and any combination thereof; said coughing pattern from a group consisting of: the frequency of coughing, the duration of individual coughs, the duration of a series of coughs, the loudness of coughs, coughing comprising wet coughs, coughing comprising dry coughs, the time of day of the coughing, the movement pattern of the equine at the time of the coughing, and any combination thereof; (d) selecting said sound pattern in said equine's environment from a group consisting of: breathing, hoof sounds, neighing, whinnying, squealing, snorting, sighing, otherwise vocalizing, eating, moving, urinating, defecating, non-equine animal vocalizing, footsteps, human speech, human whistling, human humming, human singing, mechanical sounds, weather sounds, and any combination thereof; selecting said non-equine animal vocalizing from a group consisting of: barking, growling, yapping, meowing, purring, hissing, mooing, lowing, groaning, and any combination thereof.

11. The method of claim 10, additionally comprising steps of: (a) determining, from said at least one parameter, a pattern of abnormal equine condition; (b) selecting said pattern of abnormal equine condition from a group consisting of: abnormal sweating, temperature too high, temperature too low, oxygen level too high, oxygen level too low, $CO_2$ level too low, $CO_2$ level too high, rearing, bucking, moving too much, moving too little, eating too much, eating too little, eating too fast, eating too slowly, chewing objects other than food, biting objects other than food, chewing without eating, drinking too much, drinking too little, drinking too fast, drinking too slowly, uttering an abnormal coughing pattern, an abnormal sound pattern in said equine's environment and any combination thereof; (c) selecting said abnormal coughing pattern of said equine from a group consisting of: coughing too often, coughing too seldom, individual coughs of too short duration, individual coughs of too long duration, too short a series of coughs, too long a series of coughs, overly loud coughs, overly quiet coughs, wet coughing, persistent dry coughing, coughing at an unusual time of day, increased coughing at a particular time of day, coughing during exercise, coughing in the stable, coughing in the aftermath of exercise, coughing in the lead-up to exercise, coughing during prolonged exercise, coughing in the aftermath of prolonged exercise, coughing during prolonged exercise, coughing in the aftermath of prolonged exercise, coughing while stabled, coughing while in the pasture, wheezing and any combination thereof; (d) selecting said abnormal sound pattern in said equine's environment from a group consisting of: hooves hitting the floor too much, hooves hitting the floor too little, hooves hitting the bedding too much, hooves hitting the bedding too little, hooves hitting walls too much, hooves hitting objects too much, hooves hitting objects too little, and any combination thereof.

12. The method of claim 10, additionally comprising step of: obtaining said equine's health status from said abnormal coughing pattern of said equine; said abnormal coughing pattern is indicative of at least one selected from a group consisting of a viral infection, a bacterial infection, recovering from a bacterial infection, chronic respiratory disease, allergic reaction, accumulation of mucus, a foreign object lodged in the airway, and any combination thereof.

13. The method of claim 9, additionally comprising steps of indicating change in said equine's anxiety status from said abnormal behavior, selecting said change in said equine's anxiety status from a group consisting of raised anxiety and lowered anxiety, selecting said indicator of raised anxiety from a group consisting of: raising of the head, a general bracing of muscles, increased respiration, widening of the eye, fixation on an object, uneven twisting of facial muscles and any combination thereof and selecting said indicator of lowered anxiety from a group consisting of: the lick-chew-swallow reflex, lowering the head, blinking the eyes, blowing off held breath or giving an audible sigh, licking and chewing, relaxation about the eyes and ears and muzzle, cocking a hind leg in a relaxed rather than threatening posture, and any combination thereof.

14. The method of claim 9, additionally comprising step of providing said sensor comprising a member of a group consisting of: an accelerometer, a motion sensor, a sound sensor, an oxygen sensor, a $CO_2$ sensor, a pressure sensor, a velocity sensor, a temperature sensor, a moisture sensor, a stress sensor and any combination thereof.

15. The method of claim 9, additionally comprising step of providing said system comprising a member of a group consisting of: an ID, said ID uniquely identifying said equine; a harness, at least one second sensor in communication with said equine, and any combination thereof;

(a) said harness selected from a group consisting of: an elasticated surcingle configured to encircle the girth of said equine, a halter on said equine's head, a hoof boot, a horse rug, a saddle pad, a saddle, a fly mask, a cinch, a leg protector, a leg wrap, a leg bandage, and any combination thereof; said member of said sensing group is either permanently or reversibly attachable to said harness;

(b) said second sensor being in communication with said at least one database via at least one second wireless transmitter; said at least one database configured to store at least one environment parameter selected from a group consisting of: a parameter of said equine's environment, a parameter of said equine's environment as a function of time, and any combination thereof; said first sensor and said second sensor either separate or integrated together; said at least one first wireless transmitter and said at least one second wireless transmitter either separate or integrated together; said processing means are further configured to establish, from said at least one environment parameter from said at least one second sensor, a member of a group consisting of a normal environment of said equine, and a normal environment of said equine as a function of time, an abnormal environment of said equine identifiable from a member of a group consisting of: any deviation from said normal environment, and any said time-related deviation from said normal environment; and a trigger for said abnormal behavior is identifiable as said deviation from said normal environment or said time-related deviation from said normal environment;

(c) said warning mechanism is in wireless or wired communication with said processing means; said warning mechanism is additionally configured to provide notification of said abnormal environment; said audible alarm is selected from a group consisting of: a constant-pitch sound, a variable-pitch sound, a constant-volume sound, a ringing sound, a buzzing sound, a voice message, a variable-volume sound, and any combination thereof; said visual alarm is selected from a group consisting of: an illuminated light, a visible picture, a constant-color light, a variable-color light, a constant-brightness, a variable-brightness light, and any combination thereof; and said message is selected from a group consisting of an audible telephone message, an SMS message, a message displayed on a display and any combination thereof.

16. The method of claim 9, additionally comprising steps of locating a member of a sensing group consisting of said at least one first sensor, said at least one second sensor and any combination thereof at a place selected from a group consisting of: the girth of the equine, the head of the equine, the neck of the equine, the withers of the equine, a leg of said equine, a rump of said equine, and any combination thereof.

* * * * *